US010302927B2

(12) United States Patent
Dake et al.

(10) Patent No.: US 10,302,927 B2
(45) Date of Patent: May 28, 2019

(54) STRUCTURED ILLUMINATION MICROSCOPE, STRUCTURED ILLUMINATION METHOD, AND PROGRAM

(71) Applicant: NIKON CORPORATION, Tokyo (JP)

(72) Inventors: Fumihiro Dake, Kawasaki (JP); Ryosuke Komatsu, Yokohama (JP); Yosuke Shimizu, Fujisawa (JP)

( * ) Notice: Subject to any disclaimer, the term of this patent is extended or adjusted under 35 U.S.C. 154(b) by 125 days.

(21) Appl. No.: 15/103,646

(22) Filed: Jun. 10, 2016

(65) Prior Publication Data
US 2016/0320600 A1 Nov. 3, 2016

Related U.S. Application Data

(63) Continuation of application No. PCT/JP2014/082804, filed on Dec. 11, 2014.

(30) Foreign Application Priority Data

Dec. 12, 2013 (JP) .................................. 2013-257512

(51) Int. Cl.
H04N 7/18 (2006.01)
H04N 9/47 (2006.01)
(Continued)

(52) U.S. Cl.
CPC ......... *G02B 21/082* (2013.01); *G02B 21/008* (2013.01); *G02B 21/0032* (2013.01);
(Continued)

(58) Field of Classification Search
CPC ............ G01N 21/6458; G02B 21/0032; G02B 21/0056; G02B 21/0068; G02B 21/008;
(Continued)

(56) References Cited

U.S. PATENT DOCUMENTS 5,546,181 A * 8/1996 Kobayashi ....... G01N 21/95623
250/550
6,201,589 B1 * 3/2001 Tombling ................ G02F 1/292
349/141
(Continued)

FOREIGN PATENT DOCUMENTS

EP 2 136 233 A1 12/2009
GB 2339321 A 1/2000
(Continued)

OTHER PUBLICATIONS

Krizek et al., "Flexible structured illumination microscope with a programmable illumination array," Optics Express, vol. 20 No. 22, Oct. 22, 2012 pp. 24585-24599.*
(Continued)

*Primary Examiner* — Jessica M Prince

(57) ABSTRACT

A structured illumination microscope includes a spatial light modulator containing ferroelectric liquid crystals, an interference optical system for illuminating a specimen with an interference fringe generated by making lights from the spatial light modulator interfere with each other, a controller for applying a voltage pattern having a predetermined voltage value distribution to the ferroelectric liquid crystals, an image forming optical system for forming an image of the specimen, which has been irradiated with the interference fringe, an imaging element for generating an image by imaging the image formed by the image forming optical system, and a demodulating part for generating a demodulated image using a plurality of images, wherein the controller applies an image generation voltage pattern for generating the demodulated images and a burn-in prevention voltage pattern calculated based on the image generation voltage pattern to the ferroelectric liquid crystals.

10 Claims, 14 Drawing Sheets

(51) Int. Cl.
| | |
|---|---|
| G02B 21/08 | (2006.01) |
| G02B 21/06 | (2006.01) |
| G02B 21/00 | (2006.01) |
| G02B 21/36 | (2006.01) |
| G02B 27/58 | (2006.01) |
| G02F 1/137 | (2006.01) |
| G02F 1/29 | (2006.01) |
| H04N 5/232 | (2006.01) |
| G01N 21/64 | (2006.01) |
| G02F 1/141 | (2006.01) |
| G09G 3/36 | (2006.01) |

(52) U.S. Cl.
CPC ..... *G02B 21/0056* (2013.01); *G02B 21/0068* (2013.01); *G02B 21/06* (2013.01); *G02B 21/367* (2013.01); *G02B 27/58* (2013.01); *G02F 1/13768* (2013.01); *G02F 1/292* (2013.01); *H04N 5/232* (2013.01); *G01N 21/6458* (2013.01); *G02F 1/141* (2013.01); *G09G 3/3629* (2013.01)

(58) Field of Classification Search
CPC .... G02B 21/06; G02B 21/082; G02B 21/367; G02B 27/58; G02F 1/13768; G02F 1/141; G02F 1/292; G09G 3/3629; H04N 5/232
See application file for complete search history.

(56) References Cited

U.S. PATENT DOCUMENTS

| | | |
|---|---|---|
| RE38,307 E | 11/2003 | Gustafsson et al. |
| 8,115,806 B2 | 2/2012 | Osawa et al. |
| 2002/0030674 A1* | 3/2002 | Shigeta ............... G09G 3/34 345/204 |
| 2004/0222945 A1 | 11/2004 | Taira et al. |
| 2009/0296205 A1 | 12/2009 | Ouchi |
| 2017/0276922 A1* | 9/2017 | Nomura ............... G02B 21/06 |

FOREIGN PATENT DOCUMENTS

| | | |
|---|---|---|
| JP | 2002-072252 A | 3/2002 |
| JP | 2004-001348 A | 1/2004 |
| JP | 2007-072403 A | 3/2007 |
| JP | 2007-213081 A | 8/2007 |
| WO | 2008/132976 A1 | 11/2008 |
| WO | 2013/136356 A1 | 9/2013 |

OTHER PUBLICATIONS

Mar. 10, 2017 Office Action issued in Japanese Patent Application No. 2015-552502.
Shao et al., "Super-resolution 3D microscopy of live whole cells using structured illumination," Nature Methods, vol. 8, No. 12, Dec. 2011, pp. 1044-1046.
Aug. 4, 2017 Extended Search Report issued in European Patent Application No. 14869186.8.
Mar. 14, 2017 Office Action issued in Japanese Patent Application No. 2015-552502.
Mar. 17, 2015 International Search Report issued in International Patent Application No. PCT/JP2014/082804.
Mar. 17, 2015 Written Opinion of the International Searching Authority issued in International Patent Application No. PCT/JP2014/082804.
Aug. 14, 2018 Office Action issued in Japanese Patent Application No. 2017-160651.

* cited by examiner

STRUCTURED ILLUMINATION MICROSCOPE, STRUCTURED ILLUMINATION METHOD, AND PROGRAM

CROSS-REFERENCE TO RELATED APPLICATION

This is a Continuation application of International Application No. PCT/JP2014/082804, filed on Dec. 11, 2014, which claims priority on Japanese Patent Application No. 2013-257512, filed on Dec. 12, 2013. The contents of the aforementioned applications are incorporated herein by reference.

BACKGROUND

Field of the Invention

The present invention relates to a structured illumination microscope, a structured illumination method, and a program.

Background

Within microscope apparatuses, there is a super-resolution microscope that makes possible observation exceeding the resolution of an optical system.

Structured illumination microscopy (SIM) is known as one aspect of the super-resolution microscope, wherein a super-resolution image of a specimen is generated by illuminating a specimen with spatially modulated illumination light to obtain a modulated image and demodulating the modulated image (for example, refer to U.S. Reissued Pat. Invention No. 38307). In this method, a light flux exited from a light source is branched into a plurality of light fluxes by a diffraction grating or the like, and a modulated image of the specimen is obtained by illuminating the specimen with an interference fringe, which is formed by making the light fluxes interfere with each other in the vicinity of a specimen.

SUMMARY

In the structured illumination microscope described above, using a spatial light modulator that uses ferroelectric liquid crystals as a diffraction grating or the like for branching a light flux into a plurality of light fluxes is known. By applying a drive voltage to the liquid crystal element composing the spatial light modulator, the phase of the illumination light passing through the liquid crystal element can be modulated.

Meanwhile, in a liquid crystal display apparatus using ferroelectric liquid crystals, when a drive voltage of the same symbol is continuously applied to a liquid crystal element, a phenomenon called burn-in may occur, where even if a voltage is applied to the liquid crystal element, it does not change to another stable condition. Because of this, in a liquid crystal display device using ferroelectric liquid crystals, there has been proposed a method for preventing burn-in by applying the reverse voltage of the drive voltage to the liquid crystal element.

However, in the structured illumination microscope described above, when using a spatial light modulator that uses ferroelectric liquid crystals, there exists a problem in that the imaging time is increased compared to not applying a reverse voltage, because the time during which the reverse voltage of the drive voltage is being applied to the liquid crystal element is unnecessary time for the structured illumination microscope. That is, in a structured illumination microscope as described above, there exists a problem in efficiently preventing burn-in of the liquid crystal element when using a spatial light modulator that uses ferroelectric liquid crystals.

An object of an aspect of the present invention is to provide a structured illumination microscope, structured illumination method, and program that can efficiently prevent burn-in of a liquid crystal element used as a spatial light modulator.

A structured illumination microscope according to one aspect of the present invention includes a spatial light modulator containing ferroelectric liquid crystals, an interference optical system for illuminating a specimen with an interference fringe generated by causing lights from the spatial light modulator interfere with each other, a controller for applying a voltage pattern having a predetermined voltage value distribution to the ferroelectric liquid crystals, an image forming optical system for forming an image of the specimen, which has been irradiated with the interference fringe, an imaging element for generating an image by imaging the image formed by the image forming optical system, and a demodulating part for generating a demodulated image using a plurality of images, wherein the controller applies an image generation voltage pattern for generating the demodulated images and a burn-in prevention voltage pattern calculated based on the image generation voltage pattern to the ferroelectric liquid crystals.

A structured illumination method according to one aspect of the present invention includes (a) illuminating a specimen with an interference fringe generated by causing lights from a spatial light modulator containing ferroelectric liquid crystals to interfere with each other, (b) applying a voltage pattern having a predetermined voltage value distribution to the ferroelectric liquid crystals, (c) forming an image of the specimen illuminated by the interference fringe, (d) generating an image by imaging the image formed in (c), and (e) generating a demodulated image using a plurality of the images, wherein an image generation voltage pattern for generating the demodulated image and a burn-in prevention voltage pattern calculated based on the image generation voltage pattern are applied to the ferroelectric liquid crystals in (b).

A program according to one aspect of the present invention is a program for causing a computer to execute (a) illuminating a specimen with an interference fringe generated by causing lights from a spatial light modulator containing ferroelectric liquid crystals to interfere with each other, (b) applying a voltage pattern having a predetermined voltage value distribution to the ferroelectric liquid crystals, (c) forming an image of the specimen illuminated by the interference fringe, (d) generating an image by imaging the image formed in (c), and (e) generating a demodulated image using a plurality of the images, wherein an image generation voltage pattern for generating the demodulated image and a burn-in prevention voltage pattern calculated based on the image generation voltage pattern are applied to the ferroelectric liquid crystals in (b). According to an aspect of the present invention, burn-in of a liquid crystal element used as a spatial light modulator can be efficiently prevented.

DESCRIPTION OF EMBODIMENTS

A description of 2D-Structured Illumination Microscopy (2D-SIM) and 3D-Structured Illumination Microscopy (3D-SIM) is given below, preceding the description of the present invention.

While generally, with a fluorescence microscope, the fluorescence distribution of a specimen containing a fluorescent substance is observed, with 2D-SIM, a moiré is formed from the distribution of fluorescence in the specimen and the distribution of structured illumination by illuminating a specimen using an interference fringe from the interference of two light fluxes (structured illumination). Then, by obtaining and demodulating this moiré image (modulated image), a high-resolution specimen image relating to the structure of the specimen in the direction horizontal to the specimen plane (the direction perpendicular to the optical axis) can be acquired.

Meanwhile, with 3D-SIM, because an interference fringe in the optical axis direction can be formed by illuminating the specimen using an interference fringe from the interference of three light fluxes (structured illumination), a moiré can also be generated relating to the structure of the specimen in the optical axis direction. This allows a high-resolution specimen image relating to the structure of the specimen in the optical axis direction to be acquired.

In the description of the embodiment below, 3D-SIM is used as an example in description, but is also applicable to 2D-SIM.

[First Embodiment]

The first embodiment of the present invention is described below, with reference to drawings.

Figure 1:
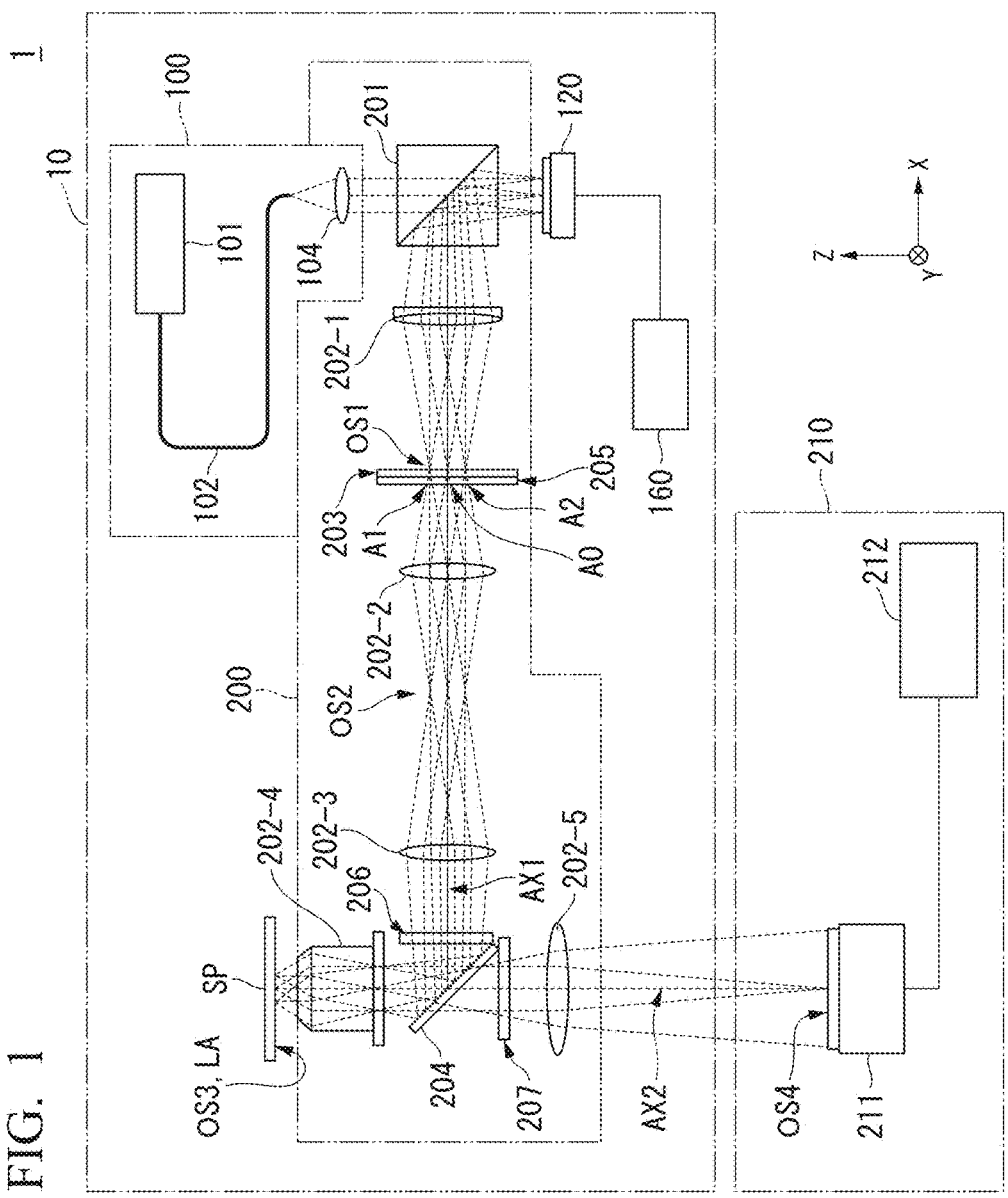
FIG. 1 is a simplified drawing illustrating the observation apparatus according to the first embodiment of the present invention.

FIG. 1 is a simplified drawing illustrating an observation apparatus 1 (structured illumination microscope) according to the first embodiment of the present invention. The observation apparatus 1 of the present embodiment is, for example, a microscope apparatus for observing a specimen SP that is a cell of a living body or the like.

In the observation apparatus 1, an illumination apparatus 10 and an imaging part 210 are provided. The illumination apparatus 10 illuminates the specimen SP with an interference fringe. The imaging part 210 images a fluorescent image of the specimen SP modulated by an interference fringe formed by an interference optical system 200, which is described hereinafter.

The illumination apparatus 10 forms an interference fringe on a predetermined illumination region LA. The specimen SP is disposed on or in the vicinity of the illumination region LA. That is, the illumination apparatus 10 forms an interference fringe on the specimen SP, along with illuminating the specimen SR In the illumination apparatus 10 according to the present embodiment, a light source apparatus 100, a light modulating part 120, a drive controller 160, and an interference optical system 200 are provided.

The light source apparatus 100 contains a light source 101, and is configured to emit a laser light at the light modulating part 120. The light modulating part 120 diffracts the entering light into a plurality of orders.

The interference optical system 200 generates an interference fringe by making a plurality of diffracted light (branched light) diffracted by the light modulating part 120 interfere with each other. Also, the interference optical system 200 forms an image of the fluorescent image of the specimen SP modulated by the interference fringe on the imaging plane of the imaging part 210. The drive controller 160 drives the light modulating part 120 and controls the phase, direction, and pitch of the interference fringe. That is, the drive controller 160 is an example of a control apparatus (controller) for applying drive voltage to the light modulating part 120. The drive controller 160 is configured from, for example, a power source apparatus and a computer or the like.

The light source apparatus 100 according to the present embodiment includes a light source 101, a light guide member 102, and a collimator 104. The light source 101 includes a light generating element (one-dimensional light source) such as a laser diode or the like, and introduces laser light to the light guide member 102. The light guide member 102 includes, for example, an optical fiber, and guides the entering light from the light source 101 to the collimator 104. Note that the exit end plane out of which the light from the light guide member 102 exits acts as a two-dimensional light source. The collimator 104 makes the light entering from the light source via the light guide member 102 into parallel light.

The interference optical system 200 according to the present embodiment includes a plurality of lens members. Specifically, in the interference optical system 200, a polarized beam splitter 201, a lens group 202, a mask 203, a dichroic mirror 204, a ½ wavelength plate 205, a filter 206, and a filter 207 are provided.

The polarized beam splitter 201 is disposed on the optical path between the collimator 104, the light modulating part 120, and the lens 202-1. The polarized beam splitter 201 passes through light that is polarized in the X direction and reflects light that is polarized in the Y direction. The polarized beam splitter 201, along with directing the light exiting from the collimator 104 to the light modulating part 120, directs one part of the light reflected by the light modulating part 120 to the lens 202-1. Here, the light exiting from the collimator 104 can be made into linear polarized light in the X direction. This allows the amount of light lost by the polarizing beam splitter 201 to be reduced. The operation of the polarizing beam splitter 201 is described hereinafter.

The mask 203 is disposed on the optical path between the lens 202-1 and the lens 202-2, and allows at least one part of the light exiting from the polarized beam splitter 201 to pass through. The mask 203 is in a plate shape, and is installed substantially perpendicular relative to the optical axis AX1.

The ½ wavelength plate 205 is disposed on the optical path between the lens 202-1 and the lens 202-2, and changes the polarization condition of the light exiting from the polarized beam splitter 201 at each direction of the structured illumination. Specifically, the ½ wavelength plate 205 converts the polarization condition of the light exiting from the polarized beam splitter 201 to S polarized light relative to the entrance plane of the light in the illumination region LA. Note that the ½ wavelength plate 205 may be installed anywhere as long as it is between the polarized beam splitter 201 and the object lens 202-4.

Lens 202-1 to 5 are included in the lens group 202. At least one from among lens 202-1 to 202-5 contains a lens member of a shape that is rotationally symmetrical around a predetermined axis of symmetry. Among these, the object lens 202-4 is a so-called object lens. Examples of this lens member include a spherical lens or an aspherical lens. In the present embodiment, the axis of symmetry of the lenses 202-1 to 202-3, which are lens members of a rotationally symmetrical shape, is appropriately called the optical axis AX1 of the interference optical system. The lens 202-1 forms an optical surface OS1. The optical surface OS1 is a conjugate plane of the rear focal point plane (pupil plane) of the object lens 202-4, and is a so-called pupil conjugate plane.

The dichroic mirror 204 is a reflection transmission member that has a different reflectivity or transmissivity according to the wavelength of the light. The dichroic mirror 204 is disposed on the optical path of the lens 202-3, the object lens 202-4, and the lens 202-5, and has a property such that at least one part of the light entering from the lens 202-3 is reflected to the direction of the object lens 202-4, and at least one part of the light entering from the object lens 202-4 is transmitted to the direction of the lens 202-5.

The filter 206 is disposed on the optical path between the lens 202-3 and the dichroic mirror 204, and transmits only excited light.

The filter 207 is disposed on the optical path between the dichroic mirror 204 and the lens 202-5, and transmits only fluorescence without transmitting excited light.

The lens 202-2 forms an optical surface OS2 with the lens 202-1, which surface is optically conjugate to the light modulating part 120. A center image of the light modulating part 120 that is illuminated by the light from the light source apparatus 100 is formed on the optical surface OS2. The lens 202-3 and the object lens 202-4 form an optical surface OS3 that is optically conjugate to the optical surface OS2. Because the optical surface OS2 is optically conjugate to the light modulating part 120, the optical surface OS3 is optically conjugate to the light modulating part 120. The illumination region LA of the illumination apparatus 10 is set on the optical surface OS3 or in the vicinity of the optical surface OS3 so that the focus accuracy of the interference fringe formed on the specimen SP is within a permissible range.

The lens 202-5 forms an optical surface OS4 that is optically conjugate to the illumination region LA. The optical surface OS4 corresponds to the image plane when the illumination region LA is the object plane. An image of the illuminated specimen SP is formed on the optical surface OS4. In the present embodiment, the object lens 202-4 and the lens 202-5 each include a lens member of a shape that is rotationally symmetrical around a predetermined axis of symmetry, and the axis of symmetry is called the optical axis AX2 of the interference optical system 200. Also, the optical axis AX2 is set practically perpendicular relative to the part of the optical axis AX1 from the lens 202-1 to 202-3 in the interference optical system 200. The plane through which the light from the specimen SP enters in the dichroic mirror 204 is slanted relative to each of the optical axis AX1 of the interference optical system 200 and the optical axis AX2 of the interference optical system 200, for example forming an angle of 45°. The light from the illuminated specimen SP enters the optical surface OS4 via the object lens 202-4, the dichroic mirror 204, and the lens 202-5.

The imaging part 210 according to the present embodiment includes an imaging element 211 and an imaging controller 212. The imaging element 211 includes an image sensor such as a CCD sensor, CMOS sensor, or the like. The imaging element 211 includes a light receiving plane on which a plurality of photodiodes is arranged, and a read circuit for reading a signal from the plurality of photodiodes. The light receiving plane of the imaging element 211 is disposed on the optical surface OS4, which is optically conjugate to the illumination region LA on which the specimen SP is disposed. The light receiving plane of the imaging element 211 may be offset from the optical surface OS4 within a range of focal depth in the direction of the optical axis AX2 of the interference optical system 200. The imaging controller 212 controls the read circuit of the imaging element 211, and along with controlling imaging timing and the like, performs calculations for generating an image of the specimen SP based on the signals from the read circuit.

The light modulating part 120 is described next in greater detail, with reference to FIGS. 2A and 2B.

Figure 2A:
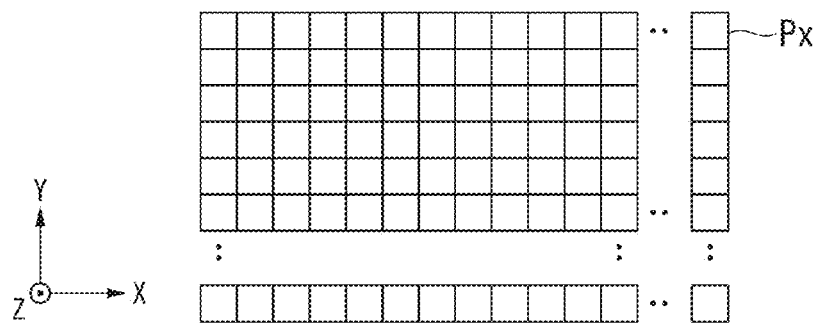
FIG. 2A is a schematic drawing illustrating an example of the configuration of the light modulating part of the present embodiment.

FIG. 2A is a schematic diagram illustrating an example of the configuration of the light modulating part 120 of the present embodiment. The light modulator 120 is provided with a spatial light modulator (SLM) that uses ferroelectric liquid crystal (FLC). The liquid crystal molecules of the ferroelectric liquid crystals have spontaneous polarization and a layer structure. The light modulating part 120 actualizes hastened switching of structured illumination by using as a diffraction grating a spatial light modulator that uses such ferroelectric liquid crystals. That is, the light modulating part 120 is an example of a branching member for branching light from the light source into a plurality of branched light. The light modulating part 120 is provided with a plurality of pixels Px disposed in a grid shape on the XY plane, which acts as a liquid crystal panel using ferroelectric liquid crystals, as illustrated in FIG. 2A. The light modulating part 120 can change the direction, phase, and pitch of the interference fringe occurring on the optical surface OS3 by changing the phase of the entering light via the voltage applied to the pixels Px.

Figure 2B:
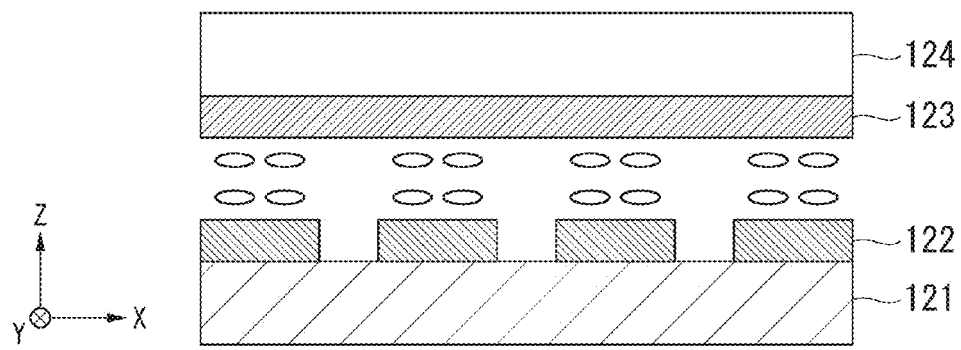
FIG. 2B is a schematic drawing illustrating an example of the configuration of the light modulating part of the present embodiment.

The light modulating part 120 has a structure wherein a first electrode substrate 121 (first substrate) is stacked on a second electrode substrate 124 in the Z axis direction, as illustrated in FIG. 2B. The first electrode substrate 121 is composed of, for example, a glass substrate, and has a pixel electrode 122 formed of, for example, silicon, on the surface thereof. There may be a circuit of, for example, TFT or the like, which is not shown, on the first electrode substrate 121. The second electrode substrate 124 is composed of, for example, a glass substrate, and has a transparent electrode 123 on the surface thereof. The light modulating part 120 applies a positive potential voltage (for example, voltage V1) or a negative potential voltage (for example, voltage –V1) to the pixel electrode 122 of the first electrode substrate 121, where the electrical potential of the transparent electrode 123 is the reference electrical potential.

Below, for the sake of convenience in description, the case where in a positive potential voltage (for example, voltage V1) is being applied to each pixel electrode 122 will be called the "white state", and for the sake of convenience in description, the case wherein a negative potential voltage (for example, voltage –V1) is being applied will be called the "black state". As is described hereinafter, the light modulating part 120 can change the phase of the reflected light at each pixel by applying a positive potential voltage or by applying a negative potential voltage to each pixel electrode 122.

The configuration of the light modulating part 120 is described in further detail. As for the spatial light modulator provided in the light modulating part 120, the molecules of the ferroelectric liquid crystals are distributed in parallel within the XY plane, and the orientation of the molecules changes to two states according to the voltage applied thereto. These two states correspond to the states of the "white state" and the "black state" described earlier. The molecules of the ferroelectric liquid crystals have a long axis and a short axis. Because the refractive index of the ferroelectric liquid crystal molecules is different in the long axis direction and the short axis direction, a different phase difference can be imparted to the light when linear polarized light enters in the long axis direction and enters in the short axis direction. That is, the spatial light modulator composing the light modulating part 120 functions as a wavelength plate that can switch its optical axis direction in two states based on the applied voltage. Also, because the spatial light modulator uses ferroelectric liquid crystals, the speed of the change in the refractive index relative to the change in voltage can be improved compared to when using, for example, nematic liquid crystals. For example, the optical axis direction can be switched to two states in microseconds.

The phase difference ΔΦ imparted by the spatial light modulator is expressed by the following equation (1), where wavelength is λ, the difference in refractive index of the long axis and the short axis of the molecule is Δn, and the element thickness is d.

[Equation 1]

$$\Delta \phi = \frac{2\pi}{\lambda} \Delta n d \quad (1)$$

Here, in the case of a reflective spatial light modulator, d is replaced with 2d. By setting so that the phase difference ΔΦ=π, the spatial light modulator functions as a λ/2 plate.

By utilizing this property, the spatial light modulator that uses ferroelectric liquid crystals can be used as an amplitude-type or a phase-type diffraction grating. A specific example of the light modulating part 120 changing the phase of the entering light is described with reference to FIG. 3A to 3C.

Figure 3A:
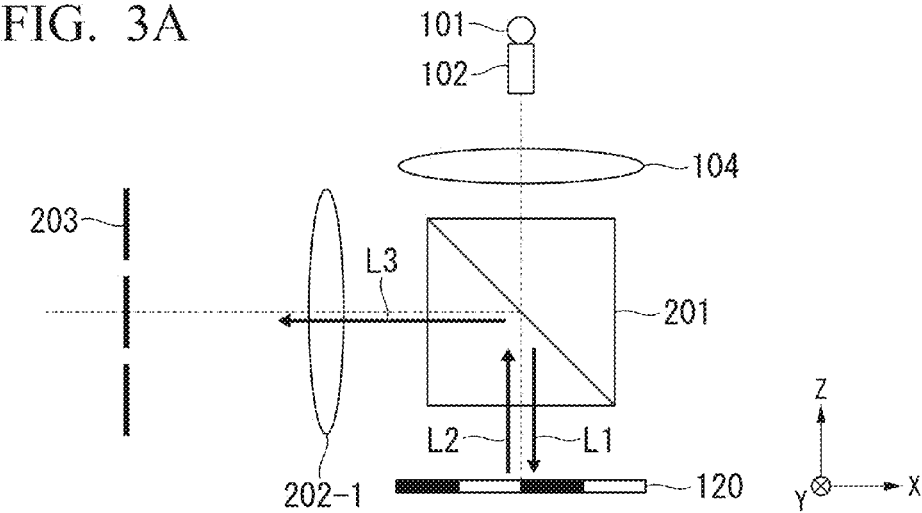
FIG. 3A is a schematic drawing illustrating an example of the phase of the light modulated by the light modulating part of the present embodiment.
Figure 3B:
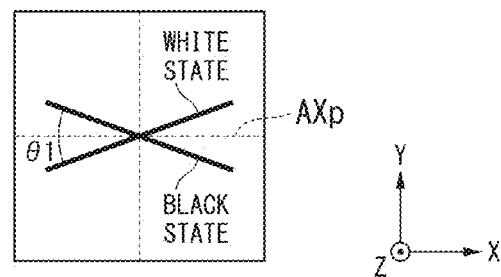
FIG. 3B is a schematic drawing illustrating an example of the phase of the light modulated by the light modulating part of the present embodiment.
Figure 3C:
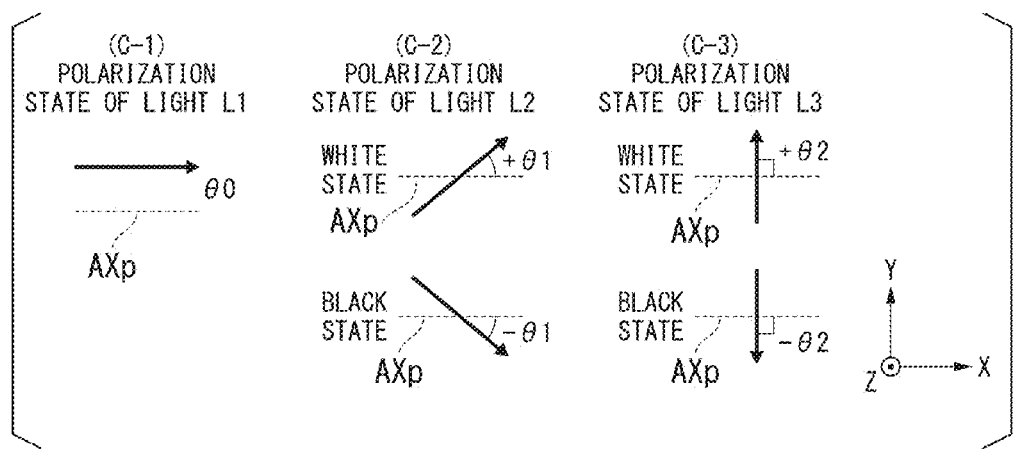
FIG. 3C is a schematic drawing illustrating an example of the phase of the light modulated by the light modulating part of the present embodiment.

FIGS. 3A to 3C are schematic drawings illustrating an example of the phase difference of the light changed by the light modulating part 120 of the present embodiment. As illustrated in FIG. 3A, a light L1, which is generated by the power source 101 and passes through the light guide member 102, the collimator 104 and the polarizing beam splitter 201, enters the light modulating part 120. The light modulating part 120 modulates the phase of the entering light L1 via the white state or the black state, and reflects a light L2. The polarizing beam splitter 201 reflects only light in a specific polarized state from among the entering light L2 as a light L3. The reflected light L3 is directed to the object lens 202-4 via the lens 202-1 and mask 203.

The modulation of the light by the light modulating part 120 is described here in detail. FIG. 3B is a conceptual drawing of the pixels Px in the light modulating part 120. In FIG. 3B, the straight line represents the long axis direction of the liquid crystal molecule. The liquid crystal molecule shows a different orientation in the white state and in the black state, as described above. Let the difference in angle between the two directions of the liquid crystal molecule be θ1; the direction of the bisector of θ1 is defined as polarizing axis AX. As illustrated in FIG. 3C (C-1), a case wherein the polarization state of the light L1 entering the light modulating part 120 is parallel to the polarizing axis AXp, that is, a case wherein the angle formed between the polarization direction of the light L1 and the polarizing axis AXp (angle θ0) is 0 (zero) [degrees] is described below.

Also, let the phase difference ΔΦ=π. At this time, the light modulating part 120 in the white state rotates the polarization direction of the entering light by angle θ1 in the counterclockwise direction relative to the polarization axis AXp. Also, the light modulating part 120, when in the black state, rotates the polarization direction of the entering light by angle θ1 in the clockwise direction relative to the polarization axis AXp (see FIG. 3C (C-2)). That is, the angular difference between the light L2 in the white state and the light L2 in the black state is made angle 2θ1 by the light modulating part 120. Here, the polarized light is vector decomposed, and an X polarized light component and a Y polarized light component are considered. The Y polarized light component has a phase difference π [rad] at a pixel in the white state and in the black state. That is, for the Y polarized light component, the light modulating part 120 is seen as a diffraction grating with phase difference π [rad]. Thus, ±1st order diffracted light, as well as high-order diffracted light is generated by the light modulating part 120. Meanwhile, for the X polarized light component, the phase difference at a pixel in the white state and the black state is zero. In this case, only 0th-order diffracted light is generated as diffracted light from the light modulating part 120. The polarizing beam splitter 201 reflects only the Y polarized light component from the entering light L2, and directs it to the lens 202-1. Thus, concerning the light L2 in the white state, light of angle θ2 corresponding to the Y component of the light of angle θ1 is selected, and concerning the light L2 in the black state, light of angle −θ2 corresponding to the Y component of the light of angle −θ1 is selected (see FIG. 3C (C-3)). Because of this, in the white state and the black state, the phase difference of the polarization state of the light L3 becomes π [rad]. As a result, just the light with equal polarization direction and phase difference π [rad] can be extracted from the diffracted light generated from the light modulating part 120. Polarization control is made easy because the polarization of the diffracted light is all the same. Specifically, the polarization direction of the structured illumination can be made into S polarized light relative to the entrance plane of the light in the illumination region LA in order to heighten the contrast of the interference fringe, but this polarization control is also made easy.

[Generation of Structured Illumination Light]

As described above, the light modulating part 120 modulates the entering light L1, and can function as a phase-type diffraction grating. Structured illumination can be generated by making the diffracted light exiting from the light modulating part 120 interfere with each other. The light modulating part 120 generates diffracted light including + (positive) 1st order diffracted light, 0th order diffracted light, and − (negative) 1st order diffracted light. In the description below, the direction of each diffracted light relative to the optical axis AX1 of the interference optical system 200 is appropriately named the diffraction direction.

Returning to the description of FIG. 1, the 0th order diffracted light diffracted by the light modulating part 120 is condensed by the lens 202-1 onto a point A0 on the optical surface OS1 established by its entrance angle into the lens 202-1. The +1st order diffracted light diffracted by the light modulating part 120 is condensed by the lens 202-1 onto a point A1 on the optical surface OS1 established by its entrance angle into the lens 202-1. The −1st order diffracted light diffracted by the light modulating part 120 is condensed by the lens 202-1 onto a point A2 on the optical surface OS1 established by its entrance angle into the lens 202-1. The mask 203 is installed in the vicinity of the condensing position of each diffracted light, and is configured to transmit the 0th order diffracted light, the +1st order diffracted light, and the −1st order diffracted light, and block other diffracted light.

Each diffracted light of the 0th order diffracted light and the ±1st order diffracted light passes through the mask 203 and enters the lens 202-2. Each diffracted light is condensed to their respective positions on the rear side focal point plane (pupil plane) of the object lens 202-4 by the lens 202-2 and 202-3. Each light exiting from their respective positions on the rear side focal point plane (pupil plane) of the object lens 202-4 becomes parallel light fluxes with differing angles, and exit toward the specimen SP from the object lens 202-4. Each diffracted light that has become a parallel light flux exiting from the object lens 202-4 interferes over the specimen SP disposed on the illumination region LA.

In this manner, each diffracted light interferes over the specimen SP, and an interference fringe is formed on the specimen SP.

The phase of the interference fringe from the interference of each diffracted light becomes a phase according to the phase difference of each diffracted light in the illumination region LA. In other words, by controlling the phase difference of each diffracted light, the phase of the interference fringe in the illumination region LA can be controlled.

[Image Demodulation Based on the Interference Fringe]

The imaging part 210 (demodulating part) images the specimen image (modulated image, moiré image) modulated by the interference fringe, and by demodulating the imaged moiré image, acquires a high-resolution image. The method for the imaging part 210 demodulating the moiré image is described below. As for the demodulation method, for example, the method described in U.S. Pat. No. 8,115,806 may be used, but is not limited to this method. An example of the demodulation method is described below. First, for the sake of simplicity, it is described using the demodulation method for 2D-SIM as an example.

In an optical system with point image strength distribution Pr (x), the specimen image obtained when providing illumination of a sinusoidal shape having a singular spatial frequency component K to a specimen having fluorescence density distribution Or (x) can be expressed as

[Equation 2]

$$I_r(x) = \sum_l m_l(O_r(x)\exp(ilKx + i\phi)) * P_r(x) \qquad (2)$$

Here, Φ is the phase of the structured illumination.

Here, l=−1, 0, and 1, and ml is the modulation amplitude of the illumination light. The l=0 component is a 0th order component that does not receive modulation from the structured illumination, and the l=−1,1 components are respectively the ±1st order components (moiré) having received modulation. In equation (2), the symbol * represents convolutional integration. Below, amounts in real space are given the subscript r, and amounts in frequency space are given the subscript k. Fourier transforming the equation (2) and writing in frequency space gives

[Equation 3]

$$I_k(k) = \sum_l m_l \exp(il\phi) O_k(k + lK) P_k(k) \qquad (3)$$

In equation (3), the Fourier transform of Pr (x), which is Pk (k), represents the optical transfer function (OTF).

Ok (k−K) and Ok (k+K) corresponding to l=−1 and 1 in equation (3) denote that the spatial frequency component of the specimen is offset by the spatial frequency component K of the structured illumination. That is, even with an optical system that can only obtain through to a spatial frequency component k, a higher spatial frequency component of the specimen can be obtained. Because of this, the period of the interference fringe can be made as short as possible within the range that an image can be formed by the optical system.

At this point, by imaging while offsetting the fringe pattern of the interference fringe, N images with the same spatial frequency component and modulation amplitude with only a different phase Φ can be obtained. The jth image signal strength lkj (k) is, with Φj as the structured illumination phase of the jth image,

[Equation 4]

$$I_{kj}(k) = \sum_{l} m_l \exp(il\phi_j) O_k(k+lK) P_k(k) \quad (4)$$

That is, an N number of equations can be acquired from equation (4). Here, because $O_k(k+lK)$, ($l=-1,0,1$) are unknown numbers in these equations, these equations can be solved if $N \geq 3$.

Here, because the detectable range of $P_k(k)$ of the optical system when providing an illumination with no strength distribution is $k=-2NA/\lambda$, to $2NA/\lambda$, relating to the optical wavelength $\lambda$ and the NA of the object lens, the $O_k(k+lK)$ obtained above in relation to $l=-1, 0$, and $1$ includes the information $k=-2NA/\lambda-K$ to $2NA/\lambda-K$, $k=2NA/\lambda$ to $2NA/\lambda$, and $k=-2NA/\lambda+K$ to $2NA/\lambda+K$. Thus, because $O_k(k+lK)$ on the whole includes information from $k=-2NA/\lambda-K$ to $2NA/\lambda+K$, by redefining this as $O_k(k)$, performing a reverse Fourier transform and returning to the information in real space (an image of $O_r(x)$ of the specimen), a microscope image with high resolution can be acquired. That is, the imaging part 210 acquires a super-resolution effect by performing image demodulation via the aforementioned calculations.

The image acquired as a result has a high resolution in only the one-dimensional direction to which spatial modulation was applied. Further, by changing the direction in which spatial modulation is implemented to at least two directions, and by implementing the same treatment as in one-dimension to each direction, the imaging part 210 can acquire a microscope image with an isotropically high resolution in two-dimension directions.

Note that the imaging part 210 can also acquire a high-resolution microscope image by configuring simultaneous equations via the least-squared method relative to the spatially modulated image and solving them.

As described above, in 2D-SIM, a specimen image with high resolution in a one-dimension direction can be obtained by changing the phase of the interference fringe and obtaining at least three images in a one-dimension direction.

Above, a demodulation method of 2D-SIM was described, but in 3D-SIM, because an interference fringe from the interference of 3 light fluxes is used, components that exist in the obtained image are five components, which are a 0th order component which does not receive modulation, the ±2nd order components that act as the super-resolution components in the one-dimension direction in the plane of the specimen, and the ±1st order components that act as the super-resolution components in the optical axis direction. Thus, in 3D-SIM, because there are five unknown numbers, by obtaining at least five images, the image can be reconstructed in the same manner as described above for 2D-SIM. In 3D-SIM, in addition to the direction of the plane, super-resolution observation can be actualized in the optical axis direction.

[Example of Interference Fringe]

An example of the interference fringe formed by the interference of diffracted light controlled by the drive controller 160 is described next, with reference to FIG. 4. As described above, when the + (positive) 1st order diffracted light, 0th order diffracted light, and − (negative) 1st order diffracted light are made to interfere on the optical surface OS3, by making the pattern of the interference fringe (henceforth fringe pattern) into five patterns, a super-resolution effect can be acquired in the planar direction of the optical surface OS3 and in the direction of the optical axis AX2, that is, it becomes 3D-SIM. Each of the five patterns have the same direction and pitch as one another, and have a fringe pattern of differing phases. Note that in order to acquire a super-resolution effect, from among interference fringes formed by the interference of diffracted light from N patterns, the phase difference of neighboring fringe patterns can be made $2\pi/N$ [rad]. For example, in a case wherein there are five patterns of fringe patterns as described above, the phase difference of neighboring fringe patterns can be $2\pi/5$ [rad]. However, for only 2D-SIM, it can be made $\pi/3$ [rad]. Here, neighboring fringe patterns denote fringe patterns that are neighboring when fringe patterns are lined up so those with the smallest phase difference are next to each other. Note that considering the periodicity of the phase, the phase difference may be $2\pi(m+1/N)$ [rad] where m is an integer, but because the phase difference of all of these can be calculated to be $2\pi$ [rad] or less, the phase difference is described below as $2\pi$ [rad] or less.

Also, while the phrase "fringe pattern" was used in description above, the phase of the fringe pattern denotes the phase of the interference fringe, the direction of the fringe pattern denotes the direction of the interference fringe, and the pitch of the fringe pattern refers to the pitch of the interference fringe. This is the same for descriptions hereafter.

Figure 4:
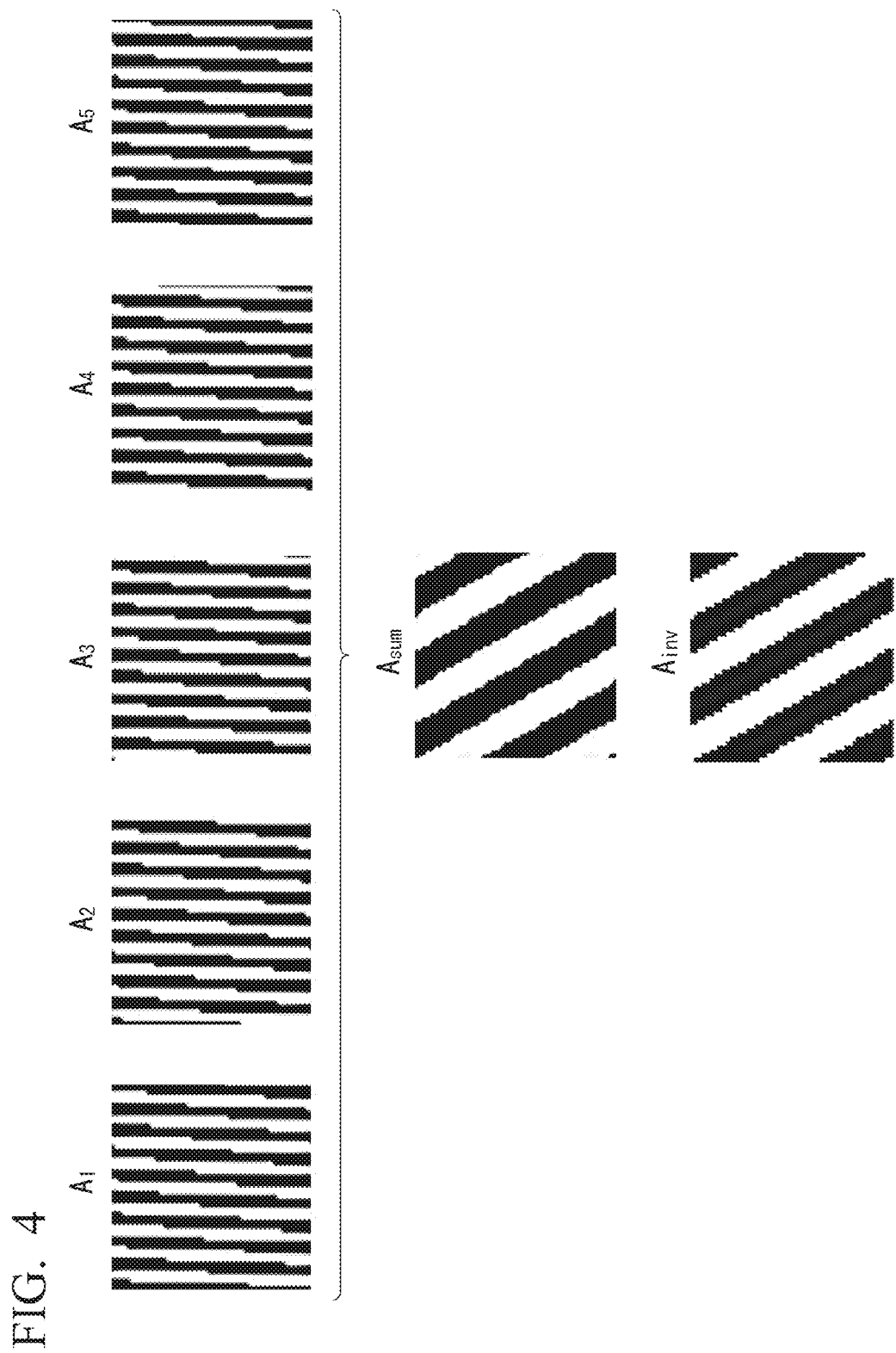
FIG. 4 is a schematic drawing illustrating an example of the voltage pattern applied by the drive controller of the present embodiment.

FIG. 4 is a schematic diagram illustrating an example of the voltage pattern applied by the drive controller 160 of the present embodiment. The drive controller 160 causes a fringe pattern of diffracted light on the optical surface OS3 by controlling the voltage pattern applied to each pixel Px of the light modulating part 120. Specifically, by applying the voltage patterns $A_1$ to $A_5$ (image generation voltage patterns) illustrated in FIG. 4 to the light modulating part 120, the drive controller 160 generates fringe patterns according to these voltage patterns. In FIG. 4, portions illustrated as a white color (white portions) denote the white state described above, in which a positive potential voltage (for example, voltage V1) is applied. Meanwhile, in FIG. 4, portions illustrated as a black color (black portions) denote the black state described above, in which a negative potential voltage (for example, voltage − (negative) V1) is applied. Note that a negative potential voltage may be applied to the white portions, and a positive potential voltage may be applied to the black portions. The voltage patterns in this example all have a voltage pattern for generating a fringe pattern with fringe pitch 5.3 [pixel] and fringe direction 2 [degrees]. Note that as the method for measuring angles, the 0 o'clock direction of a clock is defined as the angle $\theta$ [degrees], and the angle is defined to increase clockwise. However, the position of the angle $\theta$ [degrees] can be changed as appropriate. In this case, the fringe direction is changed accordingly. Here, the voltage pattern ratio of white portions and black portions is set as 1:1. Sequences other than this voltage pattern are described hereinafter.

These voltage patterns $A_1$ to $A_5$ are configured so the phase difference of the interference fringe formed by each neighboring voltage pattern is $2\pi/N$ [rad]. For example, the voltage pattern $A_1$ and the voltage pattern $A_2$ are configured so the phase difference of the interference fringe formed by each of them is $2\pi/5$ [rad]. Also, the voltage pattern $A_2$ and the voltage pattern $A_3$ are configured so the phase difference of the interference fringe formed by each of them is $2\pi/5$ [rad].

The drive controller 160 makes it possible to acquire a super-resolution effect in the direction of the plane of the optical surface OS3 and in the direction of the optical axis AX2 by sequentially generating these voltage patterns $A_1$ to $A_5$.

Here, when the total sum of the time of the phase difference between the first electrode substrate 121 and the second electrode substrate 124 of the light modulating part 120 is not zero, there exists a direct current component in the voltage between the first electrode substrate 121 and the second electrode substrate 124. When there is a bias in the direct current component of this voltage, due to the interior ions in the ferroelectric liquid crystals being pulled to one direction, a phenomenon called burn-in may occur, wherein they do not change to another stable state, even when applying a voltage to the liquid crystal element. Whether or not burn-in occurs between the first electrode substrate 121 and the second electrode substrate 124, and if burn-in occurs, the degree to which it does, is determined by the direct current component of the voltage applied between the electrode substrates. Thus, burn-in can be prevented by applying a reverse voltage so as to offset the direct current component of the voltage applied between the electrode substrates. Specifically, when generating the fringe pattern described above, an illumination period for illuminating light which is structured illumination and a non-illumination period for not illuminating light which is structured illumination are provided. In the non-illumination period, the light is, for example, blocked by a shutter, which is not shown. The drive controller 160 can prevent burn-in by applying a voltage that is reverse of the illumination period to the light modulating part 120 during the non-illumination period. That is, the drive controller 160 can prevent burn-in by applying a reversed pattern calculated from the plurality of voltage patterns for irradiating light that is structured light to the light modulating part 120.

Specifically, the drive controller 160 applies an inverse pattern $A_{inv}$ illustrated in FIG. 4 (burn-in prevention voltage pattern) to the light modulating part 120. Here, the inverse pattern $A_{inv}$ is the voltage pattern wherein the electrical potential of the sum voltage pattern $A_{sum}$ has been inversed. The sum voltage pattern $A_{sum}$ is the voltage pattern wherein the voltage value of each pixel in voltage patterns $A_1$ to $A_5$ have been summed at each pixel, where the white portion of the voltage patterns $A_1$ to $A_5$ are +1 and the black portions are −1. That is, the drive controller 160 applies the inverse pattern $A_{inv}$, which is the reverse voltage of the voltage pattern of the sum of the voltage patterns $A_1$ to $A_5$, to the light modulating part 120. In this manner, the drive controller 160 causes the total sum of the time of the voltage applied to the light modulating part 120 to become zero, thereby offsetting the direct current component. Because of this, the drive controller 160 is able to prevent burn-in of the light modulating part 120. At this time, the drive controller 160 applies a voltage pattern in, for example, the sequence illustrated in FIG. 5.

Figure 5:
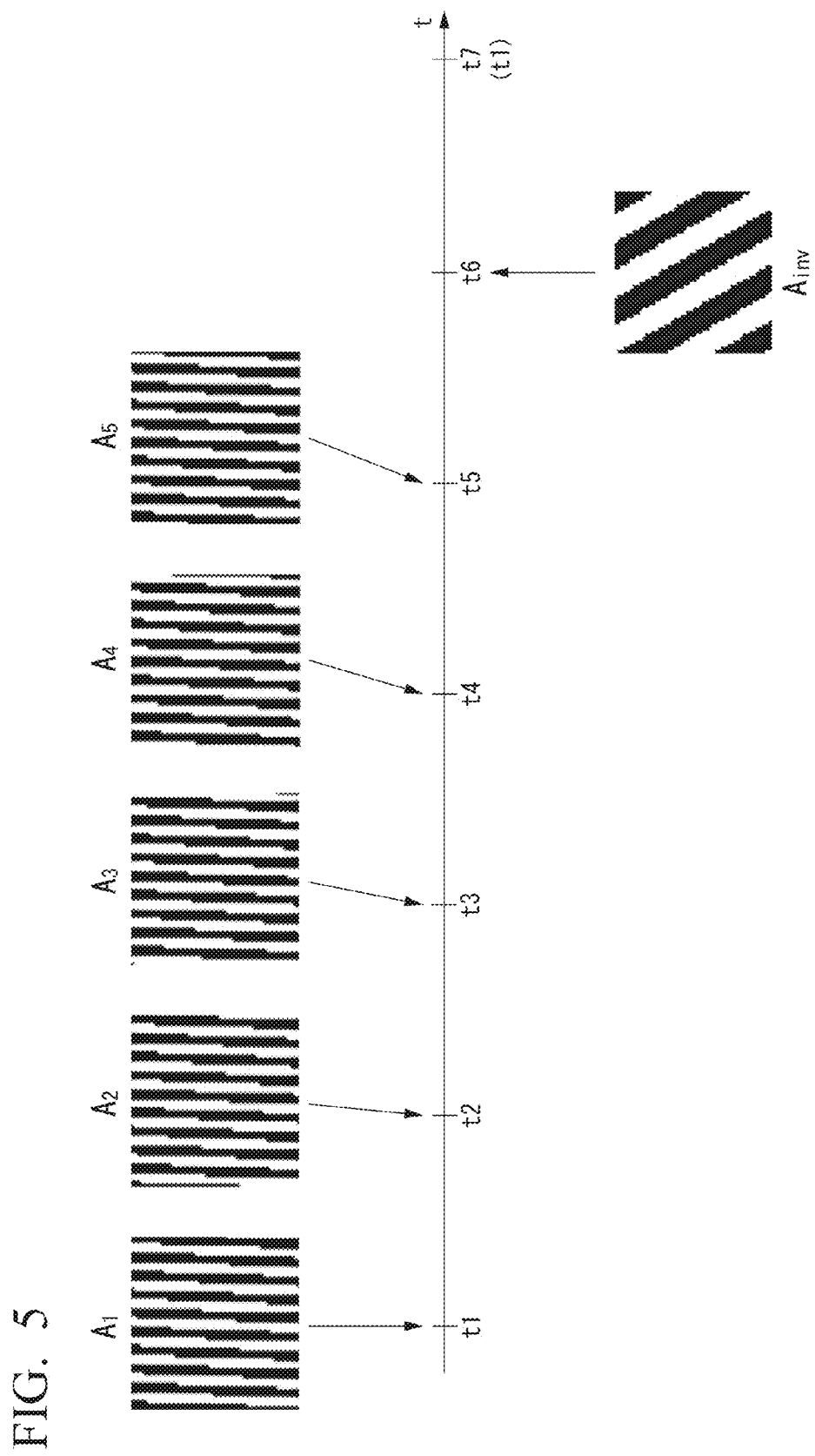
FIG. 5 is a schematic drawing illustrating an example of the sequence of the voltage pattern applied to the light modulating part by the drive controller of the present embodiment.

FIG. 5 is a schematic drawing illustrating an example of a sequence of the voltage pattern applied to the light modulating part 120 by the drive controller 160 of the present embodiment. As illustrated in FIG. 5, the drive controller 160 sequentially applies the voltage patterns $A_1$ to $A_5$ and inverse pattern $A_{inv}$ with the passage of time t. Here, let the voltage patterns $A_1$ to $A_5$ be one period of voltage pattern. In other words, one period of voltage pattern is a plurality of fringe patterns with the same direction and pitch; in the 2D-SIM described above, it is three patterns, and in 3D-SIM, it is five patterns. The drive controller 160 applies voltage pattern $A_1$ from time t1 to t2. Then, the drive controller 160 applies voltage pattern A2 from time t2 to t3.

In this manner, the drive controller 160 sequentially applies voltage patterns $A_3$ to $A_5$ during time t3 to t6. Also, the drive controller 160 applies the inverse pattern $A_{inv}$ during the non-irradiation period, where time t6 to t7 is the non-irradiation period. By sequentially applying the voltage patterns $A_1$ to $A_5$ and the inverse pattern $A_{inv}$ as illustrated in FIG. 5, the drive controller 160 can prevent burn-in of the light modulating part 120.

Figure 6:
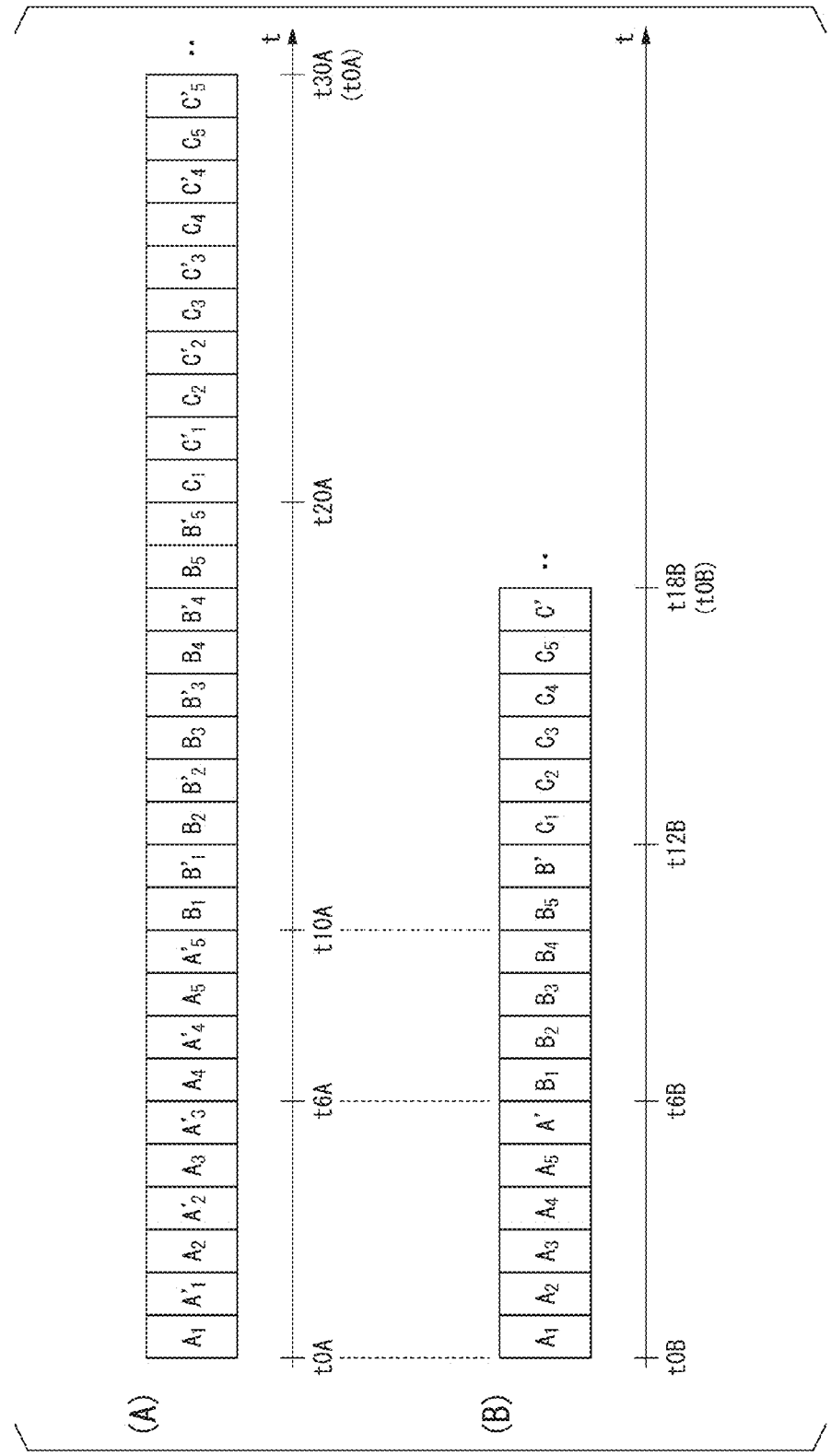
FIG. 6 is a schematic drawing illustrating a comparative example of the application sequence of the voltage pattern.

Here, with reference to FIG. 6, the application sequence of the voltage patterns according to the conventional method and the application sequence of the voltage patterns by the drive controller 160 of the present embodiment are compared and described.

FIG. 6 is a schematic drawing illustrating a comparative example of the application sequence of the voltage pattern. An application sequence that differs from that of the present embodiment is illustrated in FIG. 6 (A). According to the application sequence illustrated in FIG. 6 (A), an inverse pattern $A_1'$ relating to the voltage pattern $A_1$ is applied after voltage pattern $A_1$, that is, before the next voltage pattern $A_2$ is applied. That is, according to the application sequence illustrated in FIG. 6 (A), a voltage pattern and the inverse pattern relating to this voltage pattern are applied alternately. Here, if the time for applying one voltage pattern is T, when alternately applying a voltage pattern and its inverse pattern, the time required for applying one period of voltage pattern is the time from time t0A to time t10A, or in other words, 10T. The application sequence of the voltage pattern by the drive controller 160 of the present embodiment is illustrated in FIG. 6 (B). According to the application sequence of the voltage pattern by the drive controller 160, the inverse pattern A' relating to the sum value of voltage patterns $A_1$ to $A_5$ is applied after the voltage patterns $A_1$ to $A_5$ are applied. Here, the inverse pattern A' in FIG. 6 (B) is the inverse pattern $A_1$, described above. That is, according to the application sequence of the voltage pattern by the drive controller 160, the inverse pattern A' is applied just once after the voltage patterns $A_1$ to $A_5$ are applied. Here, when applying the inverse pattern just once after applying the voltage patterns, the time required for applying one period of voltage patterns is from time t0B to time t6B, or in other words, 6T. Thus, according to the application sequence of the voltage patterns by the drive controller 160, the time required for applying one period of voltage patterns can be reduced compared to the application sequence illustrated in FIG. 6 (A). In the case of this specific example, the time required for applying one period of voltage patterns can be reduced by approximately 40[%] with the application sequence of the voltage patterns by the drive controller 160. This allows the time required for observation by the observation apparatus 1 to be reduced by the illumination apparatus 10. In this manner, burn-in of the liquid crystal element used as a spatial light modulator can be efficiently prevented by the drive controller 160 of the present embodiment. Also, for example, when observing a living cell using the super-resolution microscope according to the embodiment of the present invention, dynamics can be observed that are faster than conventional. Thus, the super-resolution microscope according to the embodiment of the present invention is, for example, suitable for observing living cells.

[Modified Example 1]

Note that until this point, although an example was described wherein the drive controller 160 applied an inverse pattern relating to the sum value of the voltage patterns $A_1$ to $A_5$ just once after the application of the voltage patterns $A_1$ to $A_5$, it is not limited to such. The drive controller 160 may, for example, apply the voltage patterns and the inverse pattern according to the sequence illustrated in FIG. 7.

Figure 7:
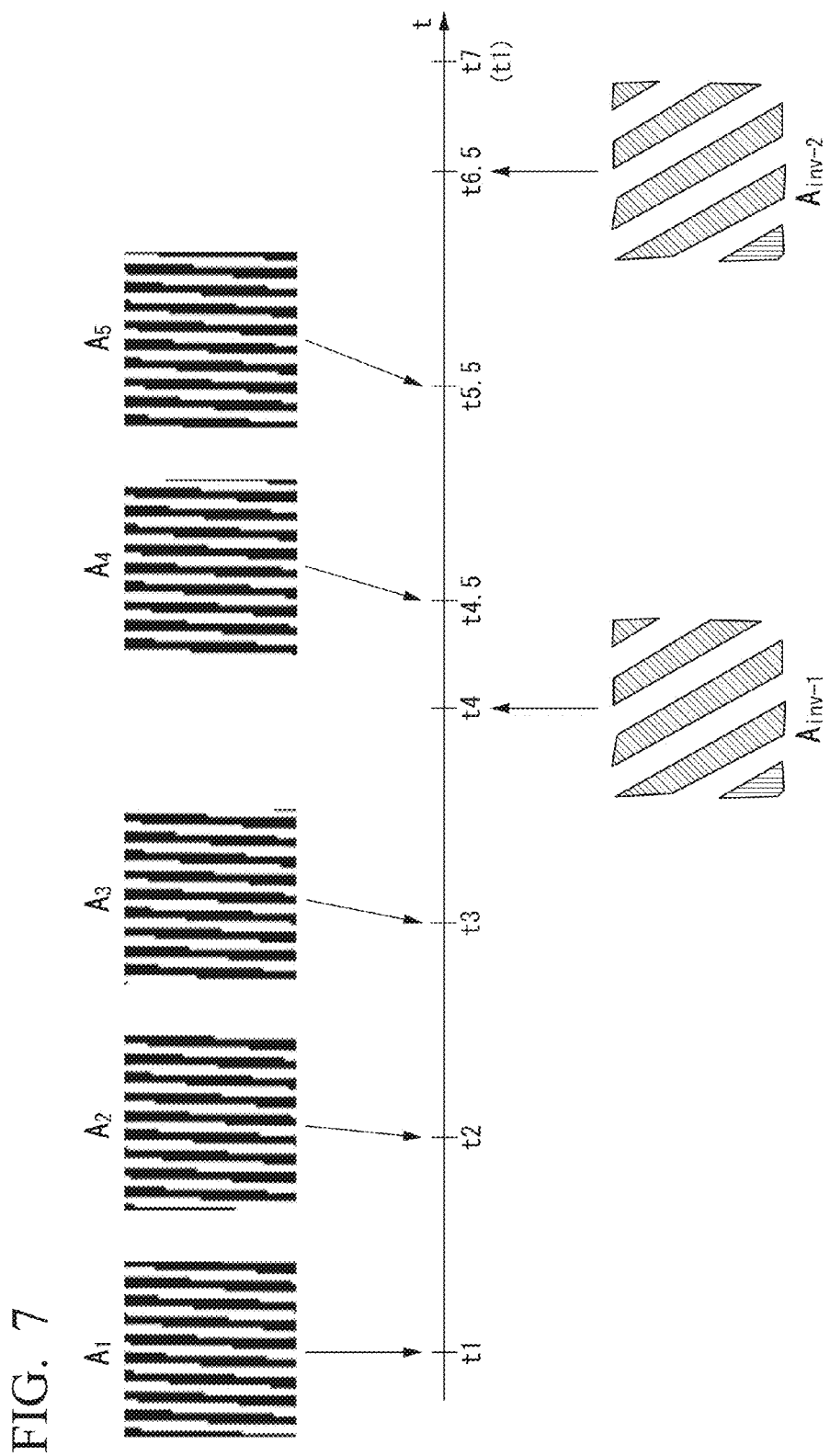
FIG. 7 is a schematic drawing illustrating a modified example of the sequence of the voltage pattern applied to the light modulating part by the drive controller of the present embodiment.

FIG. 7 is a schematic drawing illustrating a modified example of the sequence of the voltage patterns applied to the light modulating part 120 by the drive controller 160 of the present embodiment. In this modified example, the drive controller 160 applies an inverse pattern $A_{inv\text{-}1}$ (burn-in prevention voltage pattern) and an inverse pattern $A_{inv\text{-}2}$ (burn-in prevention voltage pattern) while the voltage patterns $A_1$ to $A_5$ are applied. Specifically, the drive controller 160 applies the inverse pattern $A_{inv\text{-}1}$ after applying the voltage patterns $A_1$ to $A_3$ and before applying the voltage pattern $A_4$. Then, the drive controller 160 applies the inverse pattern $A_{inv\text{-}2}$ after applying the voltage patterns $A_4$ to $A_5$ and before applying the voltage pattern $A_1$. Here, the inverse pattern $A_{inv\text{-}1}$ and the inverse pattern $A_{inv\text{-}2}$ are inverse patterns generated by equally dividing the voltage value of $A_{inv}$ illustrated in FIG. 5. Thus, this plurality of inverse patterns (here, inverse pattern $A_{inv\text{-}1}$ and inverse pattern $A_{inv\text{-}2}$) have the same electrical potential as the inverse pattern $A_{inv}$ described above when summed. For example, the inverse pattern $A_{inv\text{-}1}$ and the inverse pattern $A_{inv\text{-}2}$ are each an inverse pattern of half the electrical potential of the inverse pattern $A_{inv}$ described above. In this modified example, the drive controller 160 applies an inverse pattern over a plurality of times in the application period of the voltage patterns $A_1$ to $A_5$. Even when applying a plurality of inverse patterns over a plurality of times in this manner, the sum value of voltage of the inverse patterns applied in one application period of voltage patterns (for example, one period) is the same voltage as in the inverse pattern $A_{inv}$ described above. This allows the direct current component from the voltage patterns A1 to A5 to be offset by inverse patterns, even when applying a plurality of inverse patterns over a plurality of times. Thus, even when applying a plurality of inverse patterns over a plurality of times, the time required for applying one period of voltage patterns can be reduced compared to the application sequence illustrated in FIG. 6 (A) described above. This allows the time required for observation by the observation apparatus 1 to be reduced by the illumination apparatus 10. In this manner, burn-in of the liquid crystal element used as a spatial light modulator can be efficiently prevented by the drive controller 160 of the present embodiment.

[Modified Example 2]

Although until this point, a case wherein the direction of the fringe pattern is one direction, that is, a case of a fringe pattern wherein the fringe pitch is 5.3 [pixel] and fringe direction is 2 [degrees] was described, it is not limited to such. Here, the observation apparatus 1 can acquire an isotropic resolution in the plane of the optical surface OS3 by observing with a fringe pattern of a plurality of fringe directions rotated in a plurality of directions. For example, the observation apparatus 1 can acquire an isotropic resolution in the plane of the optical surface OS3 by observing with a fringe pattern of three fringe directions. A modified example of the voltage pattern applied by the drive controller 160 is described with reference to FIG. 8 and FIG. 9.

Figure 8:
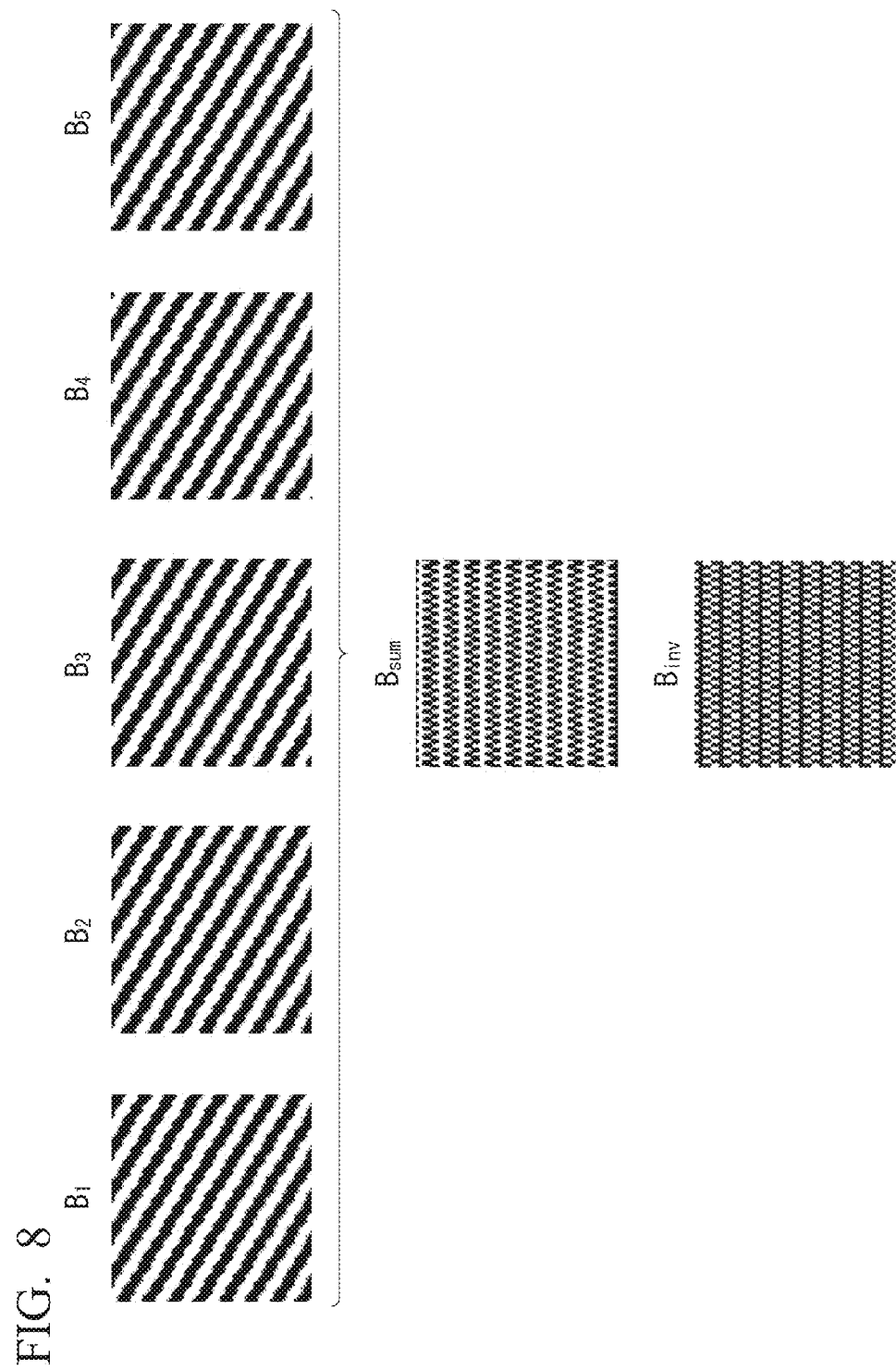
FIG. 8 is a schematic drawing illustrating the first modified example of the voltage pattern applied by the drive controller of the present embodiment.

FIG. 8 is a schematic diagram illustrating a first modified example of the voltage pattern applied by the drive controller 160 of the present embodiment. By applying the voltage patterns $B_1$ to $B_5$ (image generation voltage patterns) illustrated in FIG. 8 to the light modulating part 120, the drive controller 160 generates fringe patterns according to these voltage patterns. The voltage pattern in this modified example is a voltage pattern for generating a fringe pattern with fringe pitch 5.3 [pixel] and fringe direction −58 [degrees]. Here, the drive controller 160 applies the inverse pattern $B_{inv}$ (burn-in prevention voltage pattern) illustrated in FIG. 8 to the light modulating part 120. Here, the inverse pattern $B_{inv}$ is the voltage pattern wherein the electrical potential of the sum voltage pattern $B_{sum}$ has been inversed.

The sum voltage pattern $B_{sum}$ is the voltage pattern wherein the voltage value of each pixel in voltage patterns $B_1$ to $B_5$ have been summed at each pixel, where the white portions are +1 and the black portions are −1.

That is, the drive controller 160 applies the inverse pattern, which is the reverse voltage of the voltage pattern of the sum of the voltage patterns $B_1$ to $B_5$, to the light modulating part 120. In this manner, the drive controller 160 causes the total sum of the time of the voltage applied to the light modulating part 120 to become zero, thereby offsetting the direct current component.

Figure 9:
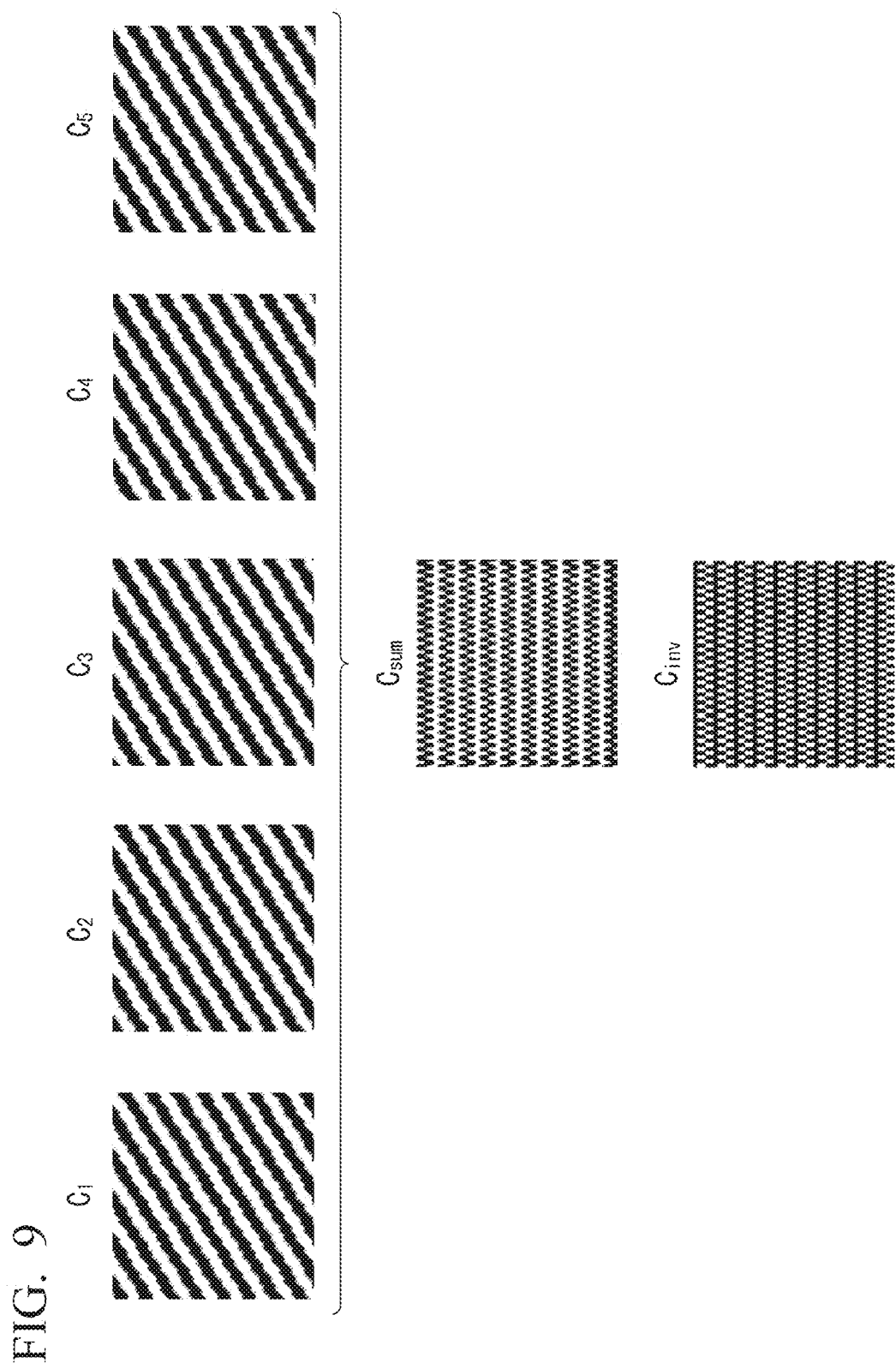
FIG. 9 is a schematic drawing illustrating the second modified example of the voltage pattern applied by the drive controller of the present embodiment.

FIG. 9 is a schematic diagram illustrating a second modified example of the voltage pattern applied by the drive controller 160 of the present embodiment. By applying the voltage patterns $C_1$ to $C_5$ (image generation voltage patterns) illustrated in FIG. 9 to the light modulating part 120, the drive controller 160 generates fringe patterns according to these voltage patterns. The voltage pattern in this modified example is a voltage pattern for generating a fringe pattern with fringe pitch 5.3 [pixel] and fringe direction 62 [degrees]. Here, the drive controller 160 applies the inverse pattern (burn-in prevention voltage pattern) illustrated in FIG. 9 to the light modulating part 120. Here, the inverse pattern $C_{inv}$ is the voltage pattern wherein the electrical potential of the sum voltage pattern $C_{sum}$ has been inversed.

The sum voltage pattern $C_{sum}$ is the voltage pattern wherein the voltage value of each pixel in voltage patterns $C_1$ to $C_5$ have been summed at each pixel, where the white portions are +1 and the black portions are −1.

That is, the drive controller 160 applies the inverse pattern which is the reverse voltage of the voltage pattern of the sum of the voltage patterns $C_1$ to $C_5$, to the light modulating part 120. In this manner, the drive controller 160 causes the total sum of the time of the voltage applied to the light modulating part 120 to become zero, thereby offsetting the direct current component.

In the case of this modified example, the drive controller 160 repeatedly applies the voltage pattern and the inverse pattern as illustrated in FIG. 6 (B). Specifically, the drive controller 160 applies the inverse pattern A' after applying the voltage patterns $A_1$ to $A_5$. Then, the drive controller 160 applies the inverse pattern B' after applying the voltage patterns $B_1$ to $B_5$. Here, the inverse pattern B' in FIG. 6 (B) is the inverse pattern $B_{inv}$ described above. Then, the drive controller 160 applies the inverse pattern C' after applying the voltage patterns $C_1$ to $C_5$. Here, the inverse pattern C' in FIG. 6 (B) is the inverse pattern $C_{inv}$ described above. Even according to this manner of application sequence, the time required for applying one period of voltage patterns can be reduced compared to the application sequence illustrated in FIG. 6 (A) above. This allows the time required for observation by the observation apparatus 1 to be reduced by the illumination apparatus 10. In this manner, burn-in of the liquid crystal element used as a spatial light modulator can be efficiently prevented by the drive controller 160 of the present embodiment.

Thus, the present invention is useful in the case of 3D-SIM, wherein an isotropic resolution can be acquired in the plane of the optical surface OS3 by observing via fringe patterns in three fringe directions.

Note that after displaying $A_1$ to $A_5$, $B_1$ to $B_5$, and $C_1$ to $C_5$, A', B', and C' may be displayed. Also, while patterns with an equal ratio of white to black in FIGS. 4, 8, and 9 were described, the present method is not limited to these. Below, the standardized ratio of white to black is defined as the duty ratio. The duty ratio=0.5 when the ratio of white to black is equal. A pattern with duty ratio 0.7 is illustrated in FIG. 10 to FIG. 12. 0th order diffracted light can be generated more efficiently by changing the duty ratio from 0.5.

Figure 10:
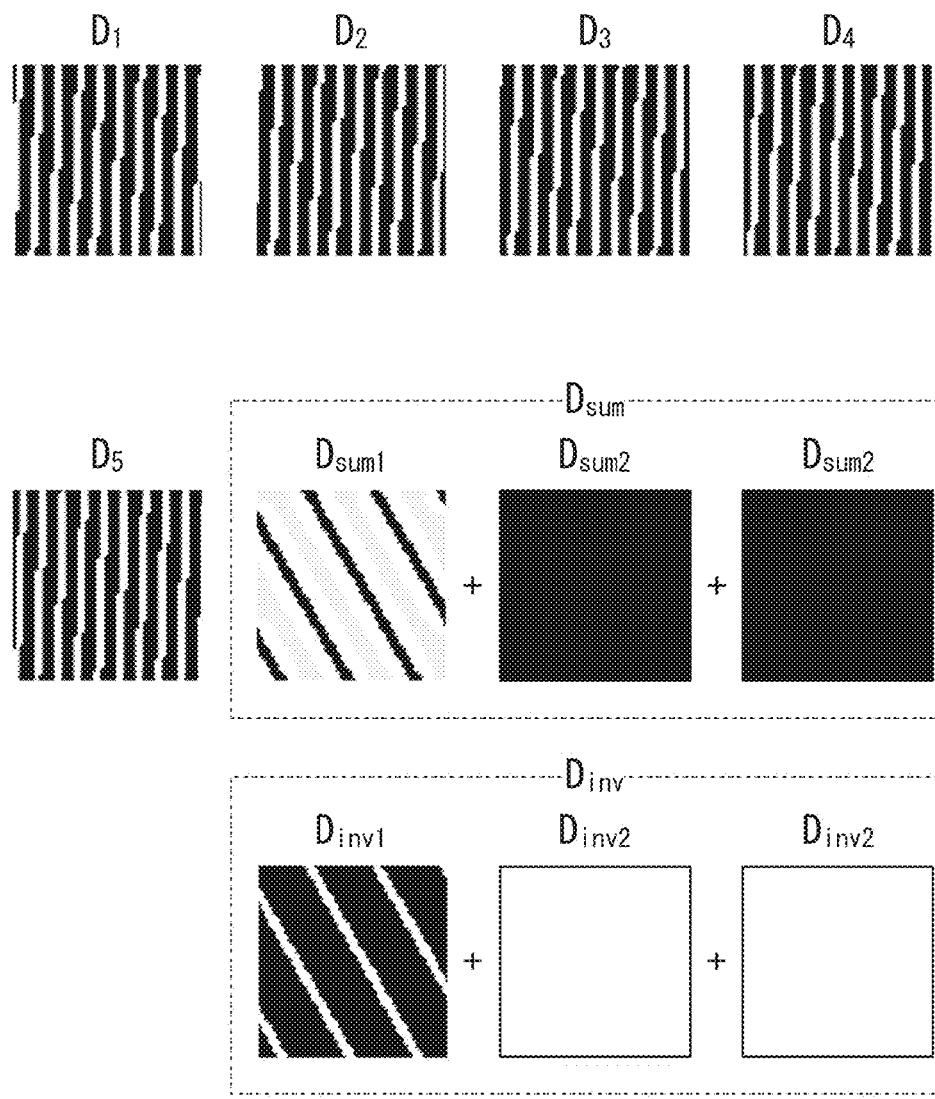
FIG. 10 is a schematic drawing illustrating the third modified example of the voltage pattern applied by the drive controller of the present embodiment.

FIG. 10 is a schematic drawing illustrating a third modified example of the voltage pattern applied by the drive controller of the present embodiment. In FIG. 10, the direction and pitch are the same as FIG. 4, and only the duty is different. Five patterns $D_1$ to $D_5$ (image generation voltage patterns) having different phases are illustrated. When the sum of each pattern is taken with black as −1 and white as +1, a two-value voltage pattern (pattern $D_{sum}$) composed of the minimum value −3 and the maximum value −1 are acquired. The pattern $D_{sum}$ is composed of the sum of one pattern $D_{sum1}$ and two patterns $D_{sum2}$. More specifically, as illustrated in FIG. 10, pattern $D_{sum1}$ is a two-value voltage pattern composed of −1 and 1, and pattern $D_{sum2}$ is a one-value voltage pattern composed of just −1. Thus, these inverse patterns are defined as pattern $D_{inv1}$ (burn-in prevention voltage pattern) and $D_{inv2}$ (burn-in prevention voltage pattern), and these three patterns are displayed only for the same amount of time as each pattern of patterns $D_1$ to $D_5$. Here, the pattern $D_{sum}$ is an example of the second voltage pattern. The pattern $D_{sum}$ has one two-value voltage pattern (in this example, pattern $D_{sum1}$) having a first voltage value and a second voltage value, and a plurality of one-value voltage patterns (in this example, pattern $D_{sum2}$) having at least only one from among the first voltage value and the second voltage value.

Figure 11:
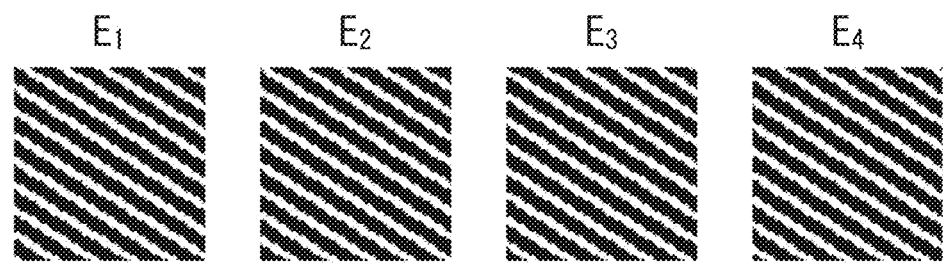
FIG. 11 is a schematic drawing illustrating the fourth modified example of the voltage pattern applied by the drive controller of the present embodiment.
Figure 11:
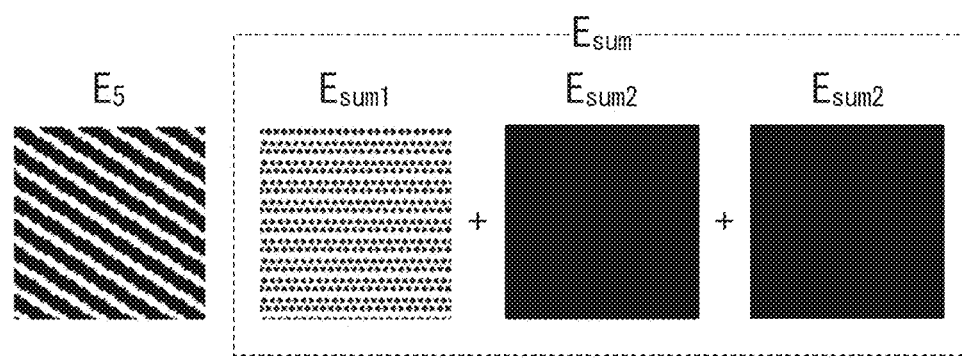
Figure 11:
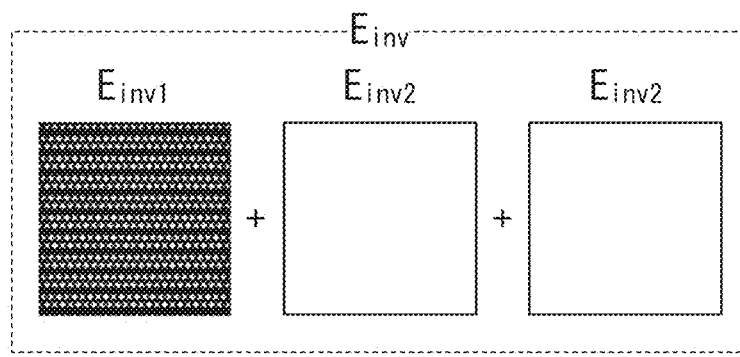

FIG. 11 is a schematic diagram illustrating a fourth modified example of the voltage pattern applied by the drive controller of the present embodiment. In FIG. 11, the direction and pitch are the same as FIG. 8, and only the duty is different. In FIG. 11, patterns $E_1$ to $E_5$ (image generation voltage patterns) are five patterns having different phases. When the sum of each pattern is taken with black as −1 and white as +1, a two-value voltage pattern (pattern $E_{sum}$) composed of the minimum value −3 and the maximum value −1 are acquired. The pattern $E_{sum}$ is composed of the sum of one pattern $E_{sum1}$ and two patterns $E_{sum2}$. More specifically, as illustrated in FIG. 11, pattern $E_{sum1}$ is a two-value voltage pattern composed of −1 and 1, and pattern $E_{sum2}$ is a one-value voltage pattern composed of just −1. Thus, these inverse patterns $E_{inv}$ (burn-in prevention voltage patterns) are composed of pattern $E_{inv1}$ and pattern $E_{inv2}$.

Figure 12:
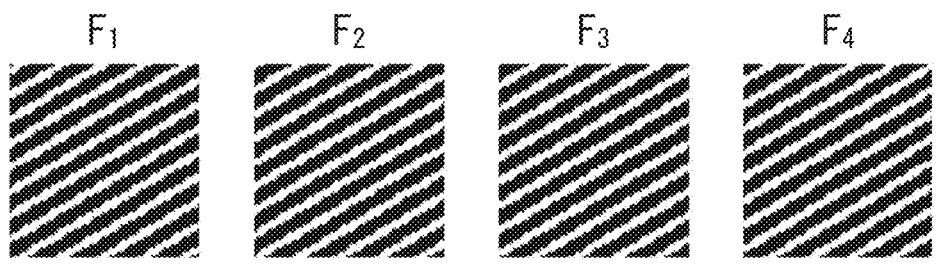
FIG. 12 is a schematic drawing illustrating the fifth modified example of the voltage pattern applied by the drive controller of the present embodiment.
Figure 12:
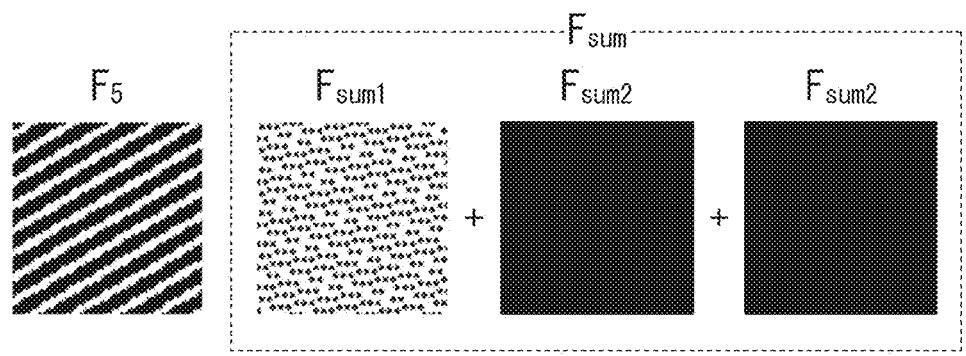
Figure 12:
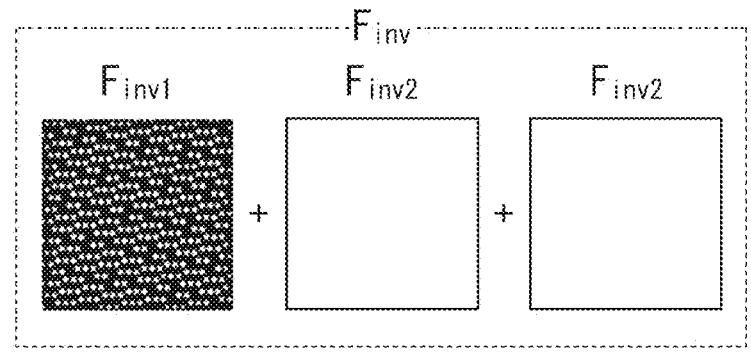

FIG. 12 is a schematic drawing illustrating a fifth modified example of the voltage pattern applied by the drive controller of the present embodiment. In FIG. 12, the direction and pitch are the same as FIG. 9, and only the duty is different. In FIG. 12, patterns $F_1$ to $F_5$ (image generation voltage patterns) are five patterns having different phases. When the sum of each pattern is taken with black as −1 and white as +1, a two-value voltage pattern (pattern $F_{sum}$) composed of the minimum value −3 and the maximum value −1 are acquired. The pattern $F_{sum}$ is composed of the sum of one pattern $F_{sum1}$ and two patterns $F_{sum2}$. More specifically, as illustrated in FIG. 12, pattern $F_{sum1}$ is a two-value voltage pattern composed of −1 and 1, and pattern $F_{sum2}$ is a one-value voltage pattern composed of just −1. Thus, these inverse patterns $F_{inv}$ (burn-in prevention voltage patterns) are composed of pattern $F_{inv1}$ and pattern $F_{inv2}$.

Here, the number of patterns with which the inverse pattern is expressed is determined by the maximum or minimum value when the sum is taken. If the absolute value of the maximum value and the minimum value are both 1, one pattern is sufficient for the inverse pattern. This corresponds to what is shown in each figure of FIG. 4, FIG. 8, and FIG. 9. If the absolute value of the maximum value or the minimum value exceeds 1, three patterns are necessary for the inverse pattern. This corresponds to what is shown in each figure of FIG. 10 to FIG. 12. The image display sequence when executing 3D-SIM with the patterns illustrated in each figure of FIG. 10 to FIG. 12 is illustrated in FIG. 13.

Figure 13:
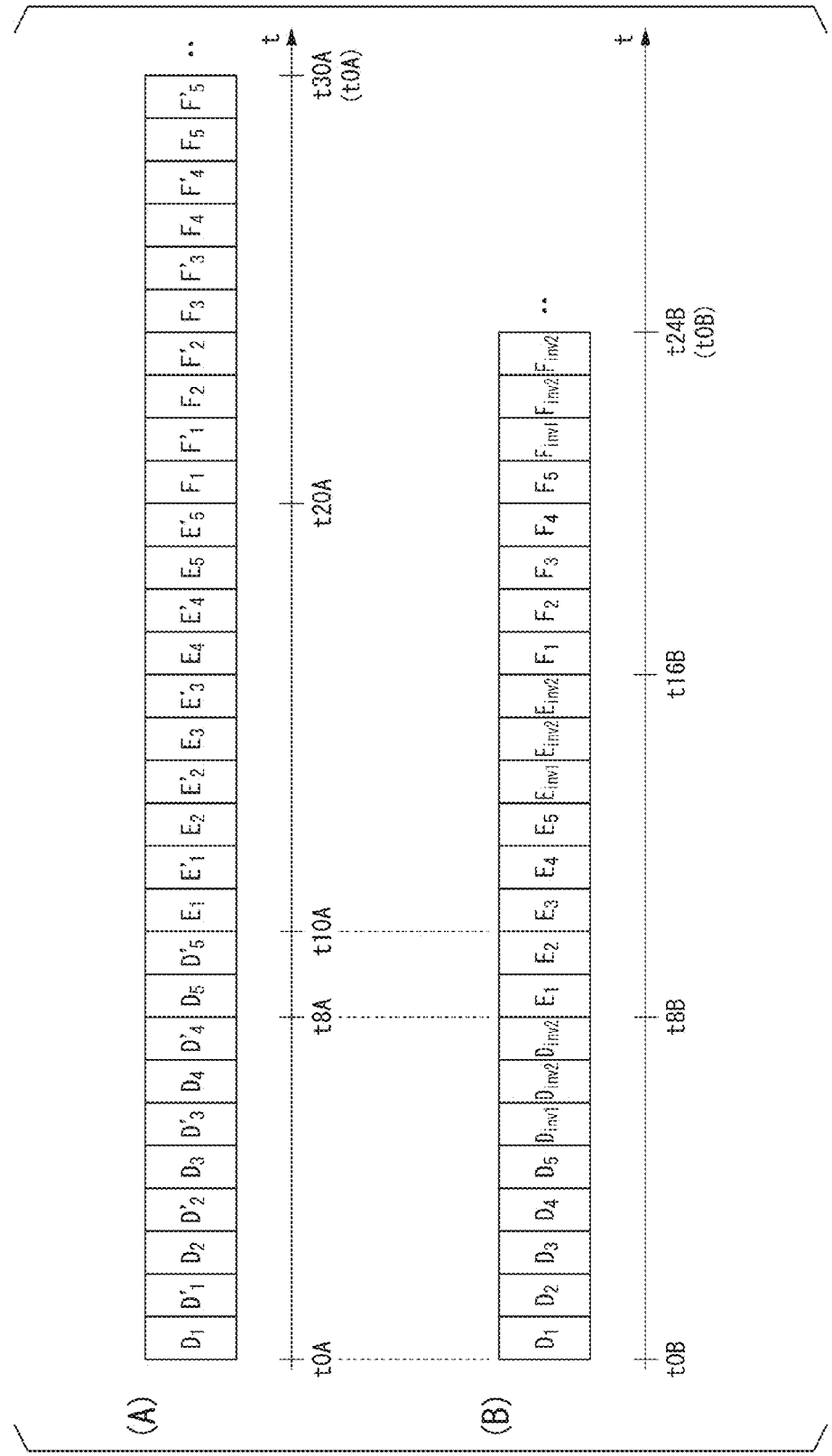
FIG. 13 is a schematic drawing illustrating a modified example of the application sequence of the voltage pattern applied by the drive controller of the present embodiment.

FIG. 13 is a schematic diagram illustrating a modified example of the application sequence of the voltage pattern applied by the drive controller of the present embodiment. FIG. 13 (A) is a case wherein an inverse pattern is displayed after each pattern, and FIG. 13 (B) is a case using the present method. By using the present method, the number of display patterns can be reduced to ⅘, allowing for the actualization of a 1.25× hastening.

The direction and pitch of the interference fringe generated by the illumination apparatus 10, that is, the measurement method of the frequency vector, is described next with reference to FIGS. 14A and 14B.

Figure 14A:
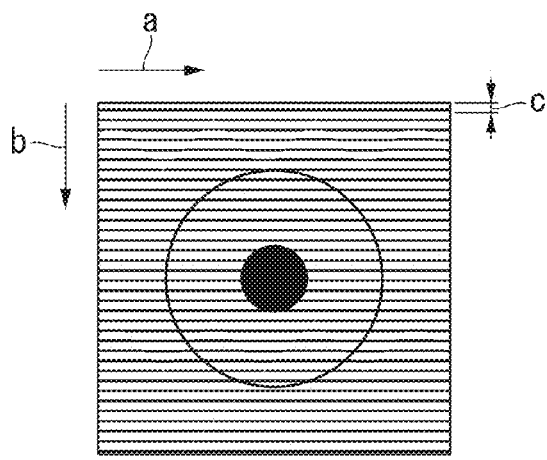
FIG. 14A is a schematic drawing illustrating an example of the interference fringe imaged by the imaging part of the present embodiment.
Figure 14B:
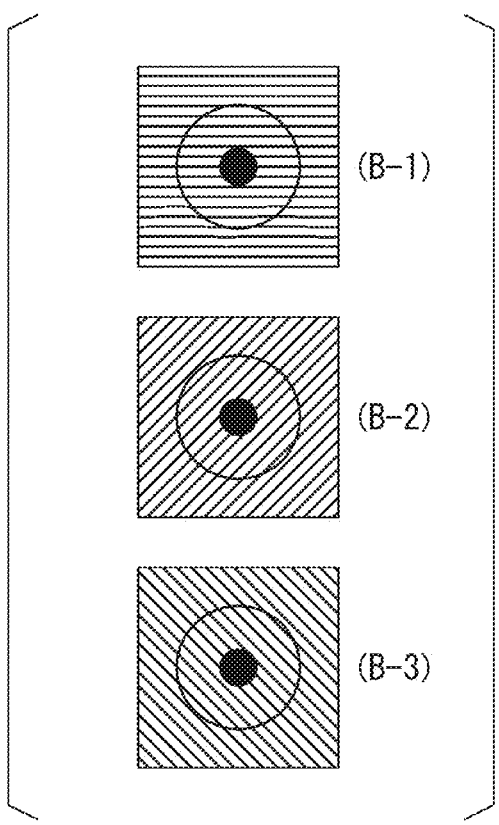
FIG. 14B is a schematic drawing illustrating an example of the interference fringe imaged by the imaging part of the present embodiment.

FIGS. 14A and 14B are schematic drawings illustrating an example of the interference fringe imaged by the imaging part 210 of the present embodiment. As described above, the imaging part 210 images an image of the interference fringe generated on the optical surface OS3, and by demodulating the imaged image, acquires a high-resolution image. At this time, for example, the imaging controller 212 can measure the direction and pitch of the interference fringe generated on the optical surface OS3, that is, the frequency vector, based on the image of the interference fringe generated on the imaged optical surface OS3. For example, as illustrated in FIG. 14B (B-1) to (B-3), even when the direction of the interference fringe changes in three directions, the imaging controller 212 can measure the frequency vector.

For example, in FIG. 14A, the arrow a illustrates the direction of the interference fringe, the arrow b illustrates the direction of the frequency vector of the interference fringe, and the arrow c illustrates the pitch of the interference fringe.

The direction and pitch of the interference fringe generated by the illumination apparatus 10, that is, the frequency vector, can also be measured in the following manner. The observation apparatus 1 can have disposed the reflective surface of a mirror ML in place of the specimen SP in the position of the optical surface OS3. The imaging part 210 images an image of the interference fringe reflected by the mirror ML. In this case, the dichroic mirror 204 can be replaced with a half mirror (not shown). At this time, for example, the imaging controller 212 can measure the direction and pitch of the interference fringe generated on the optical surface OS3, that is, the frequency vector, based on the image of the interference fringe generated on the imaged optical surface OS3.

Note that the direction (fringe direction) of the interference fringe generated when the voltage patterns A1 to A5 are applied is 2 [degrees], but an offset of direction (deflection) relative to the desired value is possible within 5 [degrees]. Also, this offset (deflection) is preferable within 2 [degrees], and more preferably within 1 [degrees]. This offset (deflection) is the same for the direction of the interference fringe generated when applying voltage patterns $B_1$ to $B_5$, and for the direction of the interference fringe generated when applying voltage patterns $C_1$ to $C_5$, as for the direction of the interference fringe caused when applying voltage patterns $A_1$ to $A_5$.

Note that in the above, the drive controller 160 was described as applying a drive voltage applied to the light modulating part 120 to all of the pixels Px provided in the light modulating part 120, but it is not limited to such. The drive controller 160 may, for example, apply a drive voltage to only pixels effective for structured illumination (effective pixels) from among all of the pixels Px provided in the light modulating part 120.

Note that in the above, an example was described wherein the voltage applied to the light modulating part 120 by the drive controller 160 was a voltage of two values, voltage V1 and voltage − (negative) V1, but it is not limited to such. The drive controller 160 may be a configuration that applies voltage other than the two values described above to the light modulating part 120. Further, the drive controller 160 was described as offsetting the direct current component with an inverse pattern from the two values of voltage based on the calculated two values of voltage, but it is not limited to such. The drive controller 160 should apply an inverse pattern that offsets the sum value of the voltage patterns. For example, when the sum value of the voltage patterns is a voltage value other than the two values described above, the drive controller 160 may offset the sum value with an inverse pattern that is the reverse voltage of a value of voltage other than the two values. Also, the drive controller 160 may be a configuration that offsets the sum value of the voltage pattern by changing the application time of the inverse pattern. For example, if the sum value of the voltage patterns is double the voltage of the voltage value of the inverse pattern, the drive controller 160 offsets the sum value of the voltage patterns by doubling the time that the inverse pattern is applied. Also, the drive controller 160 was described as applying the inverse pattern every one period of voltage patterns, but it is not limited to such. The drive controller 160 may apply an inverse pattern that is the sum value of a plurality of periods every plurality of periods of voltage patterns.

Above, an embodiment of the present invention was described in detail with reference to diagrams, but the specific configuration is not limited to this embodiment, and appropriate changes may be added within a range that does not deviate from the meaning of the present invention. The configurations described in each embodiment above may be combined.

Note that while in FIG. 1 and the like, the mask 203 is disposed on the optical path between the lens 202-1 and the lens 202-2, it may be disposed in any position between the polarizing beam splitter 201 and the illumination region LA that does not cause the optical paths of the plurality of light fluxes diffracted by the light modulating part 120 to overlap each other. For example, the mask 203 may be disposed in a position in a plane that is optically conjugate to the optical surface OS1, or the vicinity thereof.

Note that the configuration of the light source apparatus 100 may be changed as appropriate. In the embodiment above, the light source apparatus 100 is a part of the illumination apparatus 10, but at least one part of the light source apparatus 100 may be an external apparatus to the illumination apparatus 10.

Note that each lens in FIG. 1 and the like are drawn as one member, but the number of lens members of each lens may be one, or two or more. The interference optical system 200 may include a cut lens with one part of the rotationally symmetrical lens member cut, or it may include a rotationally non-symmetrical free-form lens.

Note that a case wherein the light modulating part 120 was a reflective-type was described in FIG. 1 and the like, but the light modulating part 120 may be a transmission-type.

Note that each part provided in each controller (drive controller 160, imaging controller 212) provided in the observation apparatus 1 of each embodiment may be actualized with specialized hardware, or actualized with memory and a microprocessor.

Note that each controller provided in the observation apparatus 1 may be configured from a memory and a CPU (central calculation apparatus), and actualize the function thereof by loading a program for actualizing the function of each part provided to the display apparatus to the memory and executing it.

Also, the processes of each part provided to the controller may be performed by recording a program for actualizing the function of each controller provided in the observation apparatus 1 on a readable recording medium, loading the program recorded on the recording medium onto a computer system, and executing it. Note that "computer system" as used here includes hardware such as an OS, peripheral devices, and the like.

Also, if the "computer system" is using a WWW system, it includes the home page provision environment (or the display environment).

Also, "computer readable recording medium" refers to recording apparatuses such as portable media such as a flexible disk, a magneto-optical disk, ROM, CD-ROM, and the like, and hard disks and the like that are contained in a computer system. Further, "computer readable recording medium" also includes things that retain a program for a given amount of time like a volatile memory inside a computer system that acts as the server or client when, for a short time, a program is retained dynamically like a communication line when sending a program via a network such as the internet or a communication circuit such as a phone circuit. Also, the program may be for actualizing one part of the functions described above, or may be further combined with a program for the functions described above recorded on a computer system.

In the embodiment, the structured illumination apparatus includes a first substrate on which a plurality of pixel electrodes are provided, a second substrate facing the first substrate, and ferroelectric liquid crystals interposed between the first substrate and the second substrate, and is provided with a branching member for branching light from a light source into a plurality of branched light; an interference optical system for illuminating a specimen via an interference fringe generated by causing the plurality of branched light to interfere with each other; a controller for applying a drive voltage of a drive voltage value shown by a voltage pattern to the ferroelectric liquid crystals via the plurality of pixel electrodes, wherein the voltage pattern is the distribution of drive voltage values applied to every pixel electrode; wherein a plurality of first voltage patterns with distributions differing from each other and at least one second voltage pattern based on the sum value of the plurality of the first voltage patterns is are included in the voltage pattern, and the controller sequentially applies the drive voltage of the drive voltage value shown by the plurality of the first voltage pattern and the second voltage pattern.

In the above embodiment, the first voltage pattern can be a two-value voltage pattern having a first voltage value of a positive electrical potential, and a second voltage value having the same absolute value as the first voltage value having a negative electrical potential.

In the above embodiment, the second voltage pattern can be a two-value voltage pattern having a first voltage value and a second voltage value.

In the above embodiment, the second voltage pattern can be a two-value voltage pattern having the first voltage value and the second voltage value, and it can have a plurality of one-value voltage patterns having at least only one from among the first voltage value and the second voltage value.

In the above embodiment, the second voltage pattern can be generated based on the reverse voltage of the sum value of the drive voltage value shown by the plurality of the first voltage patterns.

In the above embodiment, the pattern of the interference fringe generated by the interference optical system is determined according to the distribution of the voltage pattern and the plurality of the first voltage pattern may have a voltage pattern group composed of N of the first voltage pattern, and in the voltage pattern group, the N of the first voltage patterns can each be generated so the directions of the patterns of the interference fringes match each other.

In the above embodiment, the N of the first voltage pattern can be generated so the phase difference of the pattern of the neighboring interference fringes is $2\pi/N$.

In the above embodiment, the plurality of the first voltage pattern may have a plurality of the voltage pattern group, and the plurality of the voltage pattern group may be generated so the directions of the interference fringes are different from each other.

In the above embodiment, at least one of the second voltage pattern may be generated based on the reverse voltage of the sum value of the drive voltage value shown by the N of the first voltage pattern, and the controller may sequentially apply the drive voltage shown by each of the N of the first voltage patterns, and the drive voltage shown by the generated second voltage pattern.

In the above embodiment, the second voltage pattern may be generated based on the reverse voltage of the sum value of the drive voltage values shown by each of the first voltage patterns included in all of the voltage pattern groups, and the controller may sequentially apply the drive voltage of the drive voltage value shown by the plurality of the first voltage pattern included in the voltage pattern group for every voltage pattern group, and apply the drive voltage shown by the second voltage pattern.

In a separate embodiment, a structured illumination microscope apparatus is provided with the structured illumination apparatus described in any one of the embodiments, an imaging apparatus for imaging a modulated image of the specimen formed by forming an image of the observation light from the specimen illuminated by the interference fringe and obtaining modulated image of the specimen, and a calculation apparatus for demodulating the modulated image.

What is claimed is:

1. A structured illumination microscope, comprising:
    a spatial light modulator,
    an interference optical system for illuminating a specimen with an interference fringe,
    a controller for applying a voltage pattern having a predetermined voltage value distribution to the spatial light modulator,
    an image forming optical system for forming an image of the specimen, which has been irradiated with the interference fringe,
    an imaging element for generating an image by imaging the image formed by the image forming optical system, and
    a demodulating part for generating a demodulated image using a plurality of images, wherein
    the controller applies an image generation voltage pattern for generating the demodulated images and a burn-in prevention voltage pattern calculated based on a plurality of the image generation voltage patterns to the spatial light modulator.

2. The structured illumination microscope according to claim 1, wherein
    the burn-in prevention voltage pattern is not used for generating the demodulation image.

3. The structured illumination microscope according to claim 1, wherein
    the controller
    applies the image generation voltage pattern in a predetermined sequence to change a phase and direction of the interference fringe, and
    applies the burn-in prevention voltage pattern before and after the change in direction of the interference fringe.

4. The structured illumination microscope according to claim 1, wherein
    the burn-in prevention voltage pattern is calculated based on a reverse voltage of a sum voltage pattern that is a sum of the plurality of the image generation voltage patterns.

5. The structured illumination microscope according to claim 1, wherein
    the spatial light modulator includes a first substrate on which a plurality of pixel electrodes are provided, a second substrate facing the first substrate, and a liquid crystal arranged between the first substrate and the second substrate, and
    the controller applies the voltage pattern to the spatial light modulator via the pixel electrodes.

6. The structured illumination microscope according to claim 5, wherein
    the liquid crystal is a ferroelectric liquid crystal.

7. The structured illumination microscope according to claim 1, wherein
    the image generation voltage pattern is composed of a first voltage value having a positive electric potential and a second voltage value having a negative electric potential with the same absolute value as the first voltage value.

8. The structured illumination microscope according to claim 1, wherein
    the controller
    applies the image generation voltage pattern in a predetermined sequence to change a phase and a direction of the interference fringe, and
    applies the burn-in prevention voltage pattern after changing the direction of the interference fringe at least twice.

9. A structured illumination method, comprising:
    (a) illuminating a specimen with an interference fringe,
    (b) applying a voltage pattern having a predetermined voltage value distribution to a spatial light modulator,
    (c) forming an image the specimen illuminated by the interference fringe,
    (d) generating an image by imaging the image formed in (c), and
    (e) generating a demodulated image using a plurality of the images, wherein an image generation voltage pattern for generating the demodulated image and a burn-in prevention voltage pattern calculated based on a plurality of the image generation voltage patterns are applied to the spatial light modulator in (b).

10. A non-transitory computer readable medium storing a program for causing a computer to execute:
 (a) illuminating a specimen with an interference fringe,
 (b) applying a voltage pattern having a predetermined voltage value distribution to a spatial light modulator,
 (c) forming an image the specimen illuminated by the interference fringe,
 (d) generating an image by imaging the image formed in (c), and
 (e) generating a demodulated image using a plurality of the images, wherein an image generation voltage pattern for generating the demodulated image and a burn-in prevention voltage pattern calculated based on a plurality of the image generation voltage patterns are applied to the spatial light modulator in (b).

* * * * *